United States Patent
Hartgerink et al.

(10) Patent No.: US 12,383,653 B2
(45) Date of Patent: Aug. 12, 2025

(54) NEUTRAL MULTIDOMAIN PEPTIDE HYDROGELS AND USES THEREOF

(71) Applicant: William Marsh Rice University, Houston, TX (US)

(72) Inventors: Jeffrey Hartgerink, Houston, TX (US); David Leach, Houston, TX (US); Tania Lopez-Silva, Houston, TX (US)

(73) Assignee: William Marsh Rice University, Houston, TX (US)

( * ) Notice: Subject to any disclaimer, the term of this patent is extended or adjusted under 35 U.S.C. 154(b) by 571 days.

(21) Appl. No.: 17/285,767

(22) PCT Filed: Oct. 16, 2019

(86) PCT No.: PCT/US2019/056581
§ 371 (c)(1),
(2) Date: Apr. 15, 2021

(87) PCT Pub. No.: WO2020/081717
PCT Pub. Date: Apr. 23, 2020

(65) Prior Publication Data
US 2021/0386907 A1 Dec. 16, 2021

Related U.S. Application Data

(60) Provisional application No. 62/746,391, filed on Oct. 16, 2018.

(51) Int. Cl.
| | |
|---|---|
| *A61K 38/00* | (2006.01) |
| *A01N 1/128* | (2025.01) |
| *A61L 27/22* | (2006.01) |
| *A61L 27/52* | (2006.01) |
| *C07K 7/06* | (2006.01) |
| *C07K 7/08* | (2006.01) |
| *C12N 11/04* | (2006.01) |

(52) U.S. Cl.
CPC .............. *A61L 27/22* (2013.01); *A01N 1/128* (2025.01); *A61K 38/00* (2013.01); *A61L 27/52* (2013.01); *C07K 7/06* (2013.01); *C07K 7/08* (2013.01); *C12N 11/04* (2013.01)

(58) Field of Classification Search
CPC ....... A61L 27/22; A61L 27/52; A01N 1/0231; A61K 38/00; C07K 7/06; C07K 7/08; C12N 11/04
See application file for complete search history.

(56) References Cited

U.S. PATENT DOCUMENTS

| | | | |
|---|---|---|---|
| 5,004,681 A | 4/1991 | Boyse et al. | |
| 8,099,297 B2 | 1/2012 | Brevnova et al. | |
| 9,526,762 B1 | 12/2016 | Hartgerink et al. | |
| 2005/0106554 A1 | 5/2005 | Palecek et al. | |
| 2005/0277107 A1 | 12/2005 | Toner et al. | |
| 2008/0096809 A1* | 4/2008 | Shai | A61P 31/18 530/324 |
| 2009/0305325 A1 | 12/2009 | Kale et al. | |
| 2014/0135472 A1 | 5/2014 | King et al. | |
| 2015/0274789 A1* | 10/2015 | Guerette | A61L 27/227 524/21 |
| 2017/0172953 A1 | 6/2017 | Hartgerink et al. | |
| 2017/0335287 A1 | 11/2017 | Quarta et al. | |

FOREIGN PATENT DOCUMENTS

| | | | | |
|---|---|---|---|---|
| WO | WO 2014/104981 | | 7/2014 | |
| WO | WO 2017/009358 | * | 1/2017 | ............... C07K 7/00 |
| WO | WO 2019/018572 | | 1/2019 | |

OTHER PUBLICATIONS

Pepscan website; Available at least by Sep. 2016; Accessed online Dec. 2, 2023 at: https://www.pepscan.com/custom-peptide-synthesis/peptide-modifications/n-terminal-modifications/#:~:text=Generally%2C%20acetyl%20modification%20is%20recommended,resist%20enzymatic%20degradation%20by%20exopeptidases.*
Snyder, M. Drug Discov. & Devel. (Mar. 2017), Lyophilization: The basics; Accessed online Dec. 2, 2023 at: https://www.drugdiscoverytrends.com/lyophilization-the-basics/#:~:text=Lyophilization%20enables%20longer%20shelf%20life,easier%20to%20transport%20the%20product.*
Watanabe (Journal of Molecular Catalysis B: Enzymatic, 1998, 4, 167-180) (Year: 1998).*
Wu (Amino Acids, 2011, 40, 1053-1063) (Year: 2011).*
Bach (Appl Microbiol Biotechnol, 2013, 97, 6623-6634) (Year: 2013).*
Aggeli, A. et al., "pH as a Trigger of Peptide β-Sheet Self-Assembly and Reversible Switching between Nematic and Isotropic Phases," *J. Am. Chem. Soc.*, 125.32 (2003): 9619-9628.
Aulisa, L. et al., "Self-assembly of multidomain peptides: sequence variation allows control over cross-linking and viscoelasticity," *Biomacromolecules*, 10 (2009): 2694-2698.
Bakota, E. L. et al., "Self-Assembling Multidomain Peptide Fibers with Aromatic Cores," *Biomacromolecules*, 14.5 (2013): 1370-1378.
Bankwell, E. F. et al., "Rational design and application of responsive alpha-helical peptide hydrogels," *Nat. Mater.*, 8.7 (2009): 596-600.

(Continued)

*Primary Examiner* — Sudhakar Katakam
(74) *Attorney, Agent, or Firm* — Parker Highlander PLLC

(57) ABSTRACT

Provided herein are peptide-based hydrogels, or neutral multidomain peptide hydrogel (NMDP), as well as uses thereof. The uses include encapsulating cells to induce quiescence for long-term storage and administering to a subject to induce collagen deposition and macrophage infiltration. The disclosed hydrogel is useful for the preservation of stem cells, including maintaining their quiescence and differentiation potential.

7 Claims, 17 Drawing Sheets

Specification includes a Sequence Listing.

(56) References Cited

OTHER PUBLICATIONS

Blau, A., "Cell adhesion promotion strategies for signal transduction enhancement in microelectrode array in vitro electrophysiology: An introductory overview and critical discussion," *Current Opinion in Colloid & Interface Science*, 18.5 (2013): 481-492.

Carrejo, N. C. et al., "Multidomain Peptide Hydrogel Accelerates Healing of Full-Thickness Wounds in Diabetic Mice," *ACS Biomater Sci. Eng.*, 4.4 (2018): 1386-1396.

Chockalingam, K. et al., "Design and application of stimulus-responsive peptide systems," *Protein Engineering, Design and Selection*, 20.4 (2007) : 155-161.

Collier, J. H. et al., "Thermally and Photochemically Triggered Self-Assembly of Peptide Hydrogels," *J. Am. Chem. Soc.*, 123.38 (2001): 9463-9464.

Cormier, A. R. et al., "Molecular Structure of RADA16-I Designer Self-Assembling Peptide Nanofibers," *ACS Nano*, 7.9 (2013) : 7562-7572.

Dong. H. et al., "Self-Assembly of Multidomain Peptides: Balancing Molecular Frustration Controls Conformation and Nanostructure," *Journal of the American Chemical Society*, 129 (2007): 12468-12472.

Fischer, D. et al., "In vitro cytotoxicity testing of polycations: influence of polymer structure on cell viability and hemolysis," *Biomaterials*, 24.7 (2003): 1121-1131.

Habibi, N. et al., "Self-assembled peptide-based nanostructures: Smart nanomaterials toward targeted drug delivery," *Nano Today*, 11.1 (2016): 4160.

Hanna, J. et al., "Preservation of Stem Cells," *Organogenesis*, 5.3 (2009), 134-137.

Hartgerink, J. et al., "Self-Assembling Peptide Nanotubes," *J. Am. Chem. Soc.*, 118.1 (1996): 43-50.

Hartgerink, J. et al., "Self-Assembly and Mineralization of Peptide-Amphiphile Nanofibers," *Science*, 294.5547 (2001): 1684-1688.

Holmes, T. C. et al., "Extensive neurite outgrowth and active synapse formation on self-assembling peptide scaffolds," *PNAS*, 97.12 (2000): 6728-6733.

Hunt, C. J., "Cryopreservation of Human Stem Cells for Clinical Application: A Review," *Transfus Med Hemather*, 38 (2011): 107-123.

Kadlecova, Z. et al., "Comparative Study on the In Vitro Cytotoxicity of Linear, Dendritic, and Hyperbranched Polylysine Analogues," *Biomacromolecules*, 13.10 (2012): 3127-3137.

Leach et al., "STINGel: Controlled release of a cyclic dinucleotide for enhanced cancer immunotherapy," *Biomaterials*, 163 (2018): 67-75.

Li, Y. et al., "Biodegradable Polymer Nanogels for Drug/Nucleic Acid Delivery," *Chem. Rev.*, 115.16 (2015): 8564-8608.

Li, I-C. et al., "Covalent Capture of Aligned Self-Assembling Nanofibers," *Journal of the American Chemical Society*, 139 (2017): 8044-8050.

Lopez-Silva, T. L. et al., "Self-Assembling Multidomain Peptides: Design and Characterization of Neutral Peptide-Based Materials with pH and Ionic Strength Independent Self-Assembly," *ACS Biomater Sci. Eng.*, 5.2 (2019): 977-985.

Lutolf. M. P. et al., "Synthetic biomaterials as instructive extracellular microenvironments for morphogenesis in tissue engineering," *Nature Biotechnologie*, 23.1 (2005): 47-55.

Lynn, A. D. et al., "Characterization of the in vitro macrophage response and in vivo host response to poly(ethylene glycol)-based hydrogels," *J. Biomed. Mater. Res. Part A*, 93.3 (2009): 941-953.

Mazia, D. et al., "Adhesion of cells to surfaces coated with polylysine. Applications to electron microscopy," *J. Cell*, 66.1 (1975): 198-200.

Messam, C. A. et al., "Asynchrony and commitment to die during apoptosis," *Experimental Cell Research*, 238.2 (1998): 389-398.

Meyers, S. et al., "Biocompatible and bioactive surface modifications for prolonged in vivo efficacy," *Chem. Rev.*, 112.3 (2012): 1615-1632.

Micklitsch, C. M. et al., "Zinc-triggered hydrogelation of a self-assembling β-hairpin peptide," *Angewandte Chemie—International Edition*, 50.7 (2011): 1577-1579.

Moore, A. N, et al., "Nanofibrous peptide hydrogel elicits angiogenesis and neurogenesis without drugs, proteins, or cells," *Biomaterials*, 161 (2018): 154-163.

Moore, A. N., "Self-Assembling Multidomain Peptide Nanofibers for Delivery of Bioactive Molecules and Tissue Regeneration," *Accounts of Chemical Research*, 50 (2017):714-722.

Nisbet, D. et al., "Self-assembled peptides: characterisation and in vivo response," *Biointerphases*, 7.2 (2012): 1-14.

PCT International Preliminary Report on Patentability issued in International Patent Application No. PCT/US2019/056581, dated Apr. 29, 2021.

PCT International Search Report and Written Opinion issued in International Patent Application No. PCT/US2019/056581, dated Feb. 24, 2020.

Pochan, D. J. et al., "Thermally Reversible Hydrogels via Intramolecular Folding and Consequent Self-Assembly of a de Novo Designed Peptide," *J. Am. Chem. Soc.*, 125.39 (2003): 11802-11803.

Powers, E. T. et al., "Ordered Langmuir-Blodgett films of amphiphilic β-hairpin peptides imaged by atomic force microscopy," *Angewandte Chemie—International Edition*, 41.1 (2002): 127-130.

Rad-Malekshahi, M. et al., "Biomedical Applications of Self-Assembling Peptides," *Bioconjugate Chem.*, 27.1 (2016): 3-18.

Saha, K. et al., "Technical challenges in using human induced pluripotent stem cells to model disease," *Cell Stem Cell*, 5.6 (2009): 584-595.

Saraste A., "Morphologic criteria and detection of apoptosis," *Herz*, 24.3 (1999): 189-195.

Saraste, A. et al., "Morphologic and biochemical hallmarks of apoptosis," *Cardiovascular Research*, 45.3 (2000): 528-537.

Schneider, J. P. et al., "Responsive Hydrogels from the Intramolecular Folding and Self-Assembly of a Designed Peptide," *J. Am. Chem. Soc.*, 124 (2002): 15030-15037.

Stathopulos, P. B. et al., "Sonication of proteins causes formation of aggregates that resemble amyloid," *Protein Science*, 13 (2004): 3017-3027.

Stupp, S. I. et al., "Supramolecular Materials: Self-Organized Nanostructures," *Science*, 276 (1997): 384-389.

Veiga, A. S. et al., "Arginine-Rich Self-Assembling Peptides as Potent Antibacterial Gels," *Biomaterials*, 33.35 (2012): 8907-8916.

Webber, M. J. et al., "Supramolecular biomaterials," *Nature Materials*, 15 (2015): 13-26.

Zhu, J., "Bioactive modification of poly(ethylene glycol) hydrogels for tissue engineering," *Biomaterials*, 31.17 (2010): 4639-4656.

* cited by examiner a) Day 3 b) Day 7 c) Day 14

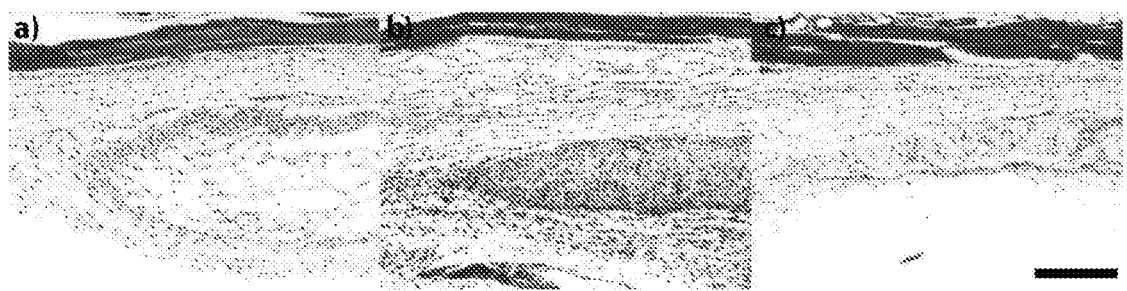
FIGS. 16A-C

NEUTRAL MULTIDOMAIN PEPTIDE HYDROGELS AND USES THEREOF

REFERENCE TO RELATED APPLICATIONS

The present application is a national phase application under 35 U.S.C. § 371 of International Application No. PCT/US2019/056581, filed Oct. 16, 2019, which claims the priority benefit of U.S. provisional application No. 62/746,391, filed Oct. 16, 2018, the entire contents of each of which are incorporated herein by reference.

STATEMENT REGARDING FEDERALLY SPONSORED RESEARCH

This invention was made with government support under Grant No. R01 DE021798 awarded by the National Institutes of Health and under Grant No. DGE1450681 awarded by the National Science Foundation. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on Oct. 1, 2019, is named RICEP0055WO_ST25.txt and is 5.7 kilobytes in size.

BACKGROUND

The development of this disclosure was funded in part by the Welch Foundation under Grant No. C-1557.

1. Field

The present invention relates generally to the fields of chemistry, cell biology, and medicine. More particularly, it concerns neutral multidomain peptide hydrogels as well as methods of use thereof.

2. Description of Related Art

Of great promise for regenerative medicine and diverse medical problems is the use of stem cells in clinical therapy. Stem cells have the capacity to differentiate into a great variety of tissues and have been shown to be effective in the treatment of autoimmune diseases, leukemia, and myocardial infarction. Despite the potential of stem cells, their therapeutic use is challenging because they can lose their potency and differentiation capacity during manipulation in vitro after isolation. In addition, the preservation of stem cells is critical for manufacturing and clinical use because it allows for the development of cell banks, the performance of quality and safety testing, transportation, long-term storage, processing, and better availability. The current methods for stem cell preservation are cryopreservation, freeze-drying, and quiescence maintenance in culture. Cryopreservation requires the use of cryopreservatives, such as DMSO, ethylenglycol, serum, and additives. On the other hand, short-term quiescence maintenance in vitro requires the use of specific medium containing a diversity of growth factors and biological cues that need to be optimized for each cell type. However, there is no universal set of conditions for preserving stem cells, and the preservation processes, preservatives, and additives used (such as DMSO) can have adverse effects that make cell recovery and protection of cell activity challenging. The development of a simple and effective preservation method for quiescent stem cells would facilitate the translation of stem cell therapies to the clinic. Therefore, compositions and methods for maintaining stem cells in quiescence, a reversible inactive state demonstrating minimal basal cell activity, are needed to allow for the preservation of these cells for prolonged periods of time.

SUMMARY

Provided here are peptide-based hydrogels, or neutral multidomain peptide hydrogel (NMDP) as well as uses thereof. When NMDP is used as a scaffold for cell encapsulation, it induces a quiescence state in cells and promotes their preservation while maintaining their viability and growing capacity over time. The chemical and physical properties of this material make it useful for the preservation of stem cells by maintaining their quiescence and differentiation potential.

In one embodiment, provided herein are compositions comprising a plurality of peptides; wherein each peptide of the plurality of peptides comprises a first domain, a second domain, and a third domain; wherein the first and third domain are each $X_m$ and m is 1-6; wherein the first domain is positioned at the N-terminal end of the second domain; wherein the third domain is positioned at the C-terminal end of the second domain; and wherein the second domain comprises alternating hydrophobic (H) and hydrophilic (p) amino acids.

In some aspects, the hydrophilic (p) amino acids are polar amino acids. In some aspects, the hydrophilic (p) amino acids are selected from the group consisting of S, T, N, and Q. In some aspects, the hydrophobic (H) amino acids are selected from the group consisting of L, I, V, A, F, Y, W, and M. In some aspects, the second domain comprises $(Hp)_n$. In some aspects, the second domain comprises $(pH)_n$. N may be 4-6. In some aspects, the second domain comprises $(SerLeu)_6$.

In some aspects, X is an amino acid that lacks hydrogens on the peptide backbone nitrogen. In some aspects, X has no potential to form beta-sheet interactions in the NMDP peptide termini. In some aspects, X is selected from the group consisting of 3'-hydroxyproline, 4'-hydroxyproline, proline, and an N-modified polar amino acid. In certain aspects, the N-modified polar amino acid is N-methylated or N-alkylated. In certain aspects, the N-modified polar amino acid is N-R-Ser, N-R-Thr, N-R-Asn, or N-R-Gln, such as, for example, those shown in Scheme 1.

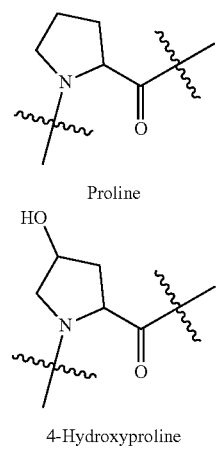

Scheme 1

Proline

4-Hydroxyproline

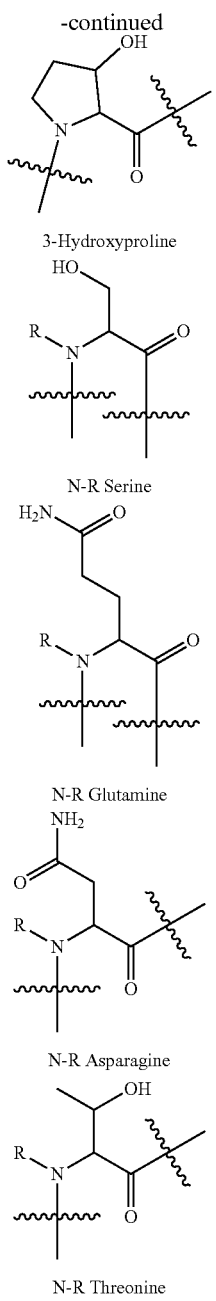

3-Hydroxyproline

N-R Serine

N-R Glutamine

N-R Asparagine

N-R Threonine

In some aspects, the peptides are N-terminally acetylated. In some aspects, the peptides are produced using solid-phase synthesis. In some aspects, m is 1, 2, 3, 4, 5, or 6. In some aspects, the sequence of each peptide comprises any one of SEQ ID NOs: 1-6.

In some aspects, the peptides further comprise a biologically active peptide mimic. In certain aspects, the biologically active peptide is attached to the N-terminus of the peptides. In certain aspects, the biologically active peptide is attached to the C-terminus of the peptides. In some aspects, the peptides further comprise a glycine spacer positioned between the peptide and the biologically active peptide mimic. In certain aspects, the glycine space comprises between one and three glycine residues. In certain aspects, the biologically active peptide mimic has a sequence selected from the group consisting of one of SED ID NOs:

10-20. In certain aspects, the biologically active peptide mimic is selected from those presented in Table 1.

TABLE 1

Biologically active peptide mimics

| Peptide mimic sequence | SEQ ID NO: | Origin | Bioactivity |
|---|---|---|---|
| RGDS | 10 | Fibronectin | Cell attachment |
| IKVAV | 11 | Laminin | Neurite outgrowth |
| KDI | 12 | Laminin-gamma 1 | Neurite outgrowth |
| RNIAEIIKDI | 13 | Laminin-gamma 1 | Neurite outgrowth |
| VFDNFVLK | 14 | Tenascin-C | Neurite outgrowth |
| DWIVA | 15 | BMP-2 | Bone formation |
| AQFHRHKQLIRFLKRA | 16 | IL-4 | Anti-inflammatory |
| RELRYLRRA | 17 | IL-4 | Anti-inflammatory |
| FLPASGL | 18 | TGF-β1 | Inflammation |
| ESPLKRQ | 19 | TGF-β1 | Inflammation |
| DPHIKLQLQAE | 20 | FGF-2 | Wound healing |

In some aspects, the composition is lyophilized. In some aspects, the compositions further comprise viable cells.

In one embodiment, provided herein is a nanofiber comprising a plurality of peptides according to any one of the present embodiments. In one embodiment, provided herein are hydrogels comprising a plurality of peptides according to any one of the present embodiments. In some aspects, the hydrogel is biocompatible. In some aspects, the hydrogel remains intact at pH 3-11. In some aspects, the hydrogel remains intact at physiological pH. In some aspects, the hydrogel has a storage modulus (G') of less than 100 Pa. In some aspects, the hydrogel has a storage modulus (G') of less than 50 Pa. In one embodiment, provided herein are methods of forming a neutral hydrogel comprising subjecting a composition of any one of the present embodiments to ultrasonication at physiological pH (7.2-7.4).

In one embodiment, provided herein are methods for inducing quiescence in cells comprising encapsulating the cells in a hydrogel of any one of the present embodiments. In some aspects, the encapsulated cells remain viable for at least five days. In some aspects, the encapsulated cells remain viable for at least 30 days. In some aspects, the methods are further defined as methods for cell preservation.

In some aspects, the cells are stem cells. In certain aspects, the stem cells are hematopoietic stem cells, mesenchymal stem cells, human embryonic stem cells, or induced-pluripotent stem cells. In some aspects, the methods maintain the differential potential of the stem cells. In some aspects, the cells do not proliferate once encapsulated in the hydrogel. In some aspects, the cells do not attach to the hydrogel.

In one embodiment, provided herein are methods comprising administering a hydrogel as provided in any one of the present embodiments to a target location in a subject. In some aspects, administering comprises injecting. In some aspects, the subject is a mammal. In some aspects, the subject is a human patient, a mouse, a rat, or a pig. In some aspects, the target location is a site comprising damaged tissue. In some aspects, the target location is a site in need of collagen deposition. In some aspects, the methods are further defined as methods for stimulating collagen deposition at a target location in a patient in need thereof. In some aspects, the methods cause macrophages to infiltrate the target location. In some aspects, the concentration of peptides in the administered hydrogel is about 3-7 mM.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the inherent variation in the method being employed to determine the value, the variation that exists among the study subjects, or a value plus or minus 5% of the stated number.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-C. Secondary structure and nanostructure characterization of $O_n(SL)_6O_n$ peptide series. FIG. 2A: ATR FTIR spectra of the amide I and amide II region of dried peptide samples. All peptides have characteristic peaks for antiparallel β-sheet structure. FIG. 2B: CD spectra of 1 wt. % ($O_1$ [top solid line at 195 nm]: 7 mM, $O_2$ [top dashed line at 195 nm]: 6 mM, $O_3$ [middle solid line at 195 nm] and $O_4$ [middle dashed line at 195 nm]: 5 mM, $O_5$ [bottom solid line at 195 nm] and $O_6$ [bottom dashed line at 195 nm]: 4 mM) peptide solutions in TFE at 25° C. FIG. 2C: Negative-stained TEM images in water. $O_1$, $O_2$, and $O_5$ at 0.01 wt. %, $O_3$, $O_4$ and $O_6$ at 0.02 wt. %. Scale bar=100 nm.

FIG. 4A: Structural characterization of 1 wt. % peptide solutions in 149 mM sucrose and 0.5×HBSS. FIG. 4B: SEM micrograph of 1 wt. % $O_5$ hydrogel showing an entangled fibrillar structure. Scale bar=1 μm. FIGS. 4C-D: Strain sweep (FIG. 4C) and shear recovery (FIG. 4D) of 1 wt. % $O_5$ peptide hydrogel.

FIGS. 5A-E. 3-D culture of NIH-3T3 fibroblasts in 1 wt. % $O_5$ hydrogel and the positively charged peptide hydrogel $K_2(SL)_6K_2$. FIG. 5A: Cell viability of NIH-3T3 fibroblasts at day 1, 3 and 5 by Calcein AM and Ethidium Homodimer-1 staining (viable cells in green, dead cells in red). Scale bar=100 μm. FIGS. 5B-C: Actin cytoskeleton staining of NIH-3T3 fibroblasts encapsulated for 5 days in $K_2$ (FIG. 5B) and $O_5$ (FIG. 5C). AlexaFluor 488-phalloidin (green) and DAPI (blue). Scale bar=50 μm. FIG. 5D: Percentage of viable cells present in $K_2$ and $O_5$ at day 1, day 3, and day 5 after seeding. FIG. 5E: Viable cell density (cells/mm$^3$) at day 1, day 3, and day 5. Error bars represent standard deviation (n=6).

FIG. 14A shows day 3, FIG. 14B shows day 7, and FIG. 14C shows day 14. After implantation, the hydrogel is infiltrated by macrophages (F4/80+ cells: dark gray, nuclei: light gray), which degrade the material and remodel the native tissue. By day 14, the implant size decreases and new collagen is observed similar to native tissue (FIG. 16C). Scale bar 100 µm. Dotted line indicates borders of the hydrogel implant.

FIGS. 16A-C. Masson's Trichome of $O_5(SL)_6O_5$ implants at day 3 (FIG. 16A), 7 (FIG. 16B), and 14 (FIG. 16C) after injection in a subcutaneous mouse model. The material is degraded and replaced by collagen similar to native tissue. Scale bar: 100 µm.

DETAILED DESCRIPTION

Figure 1:
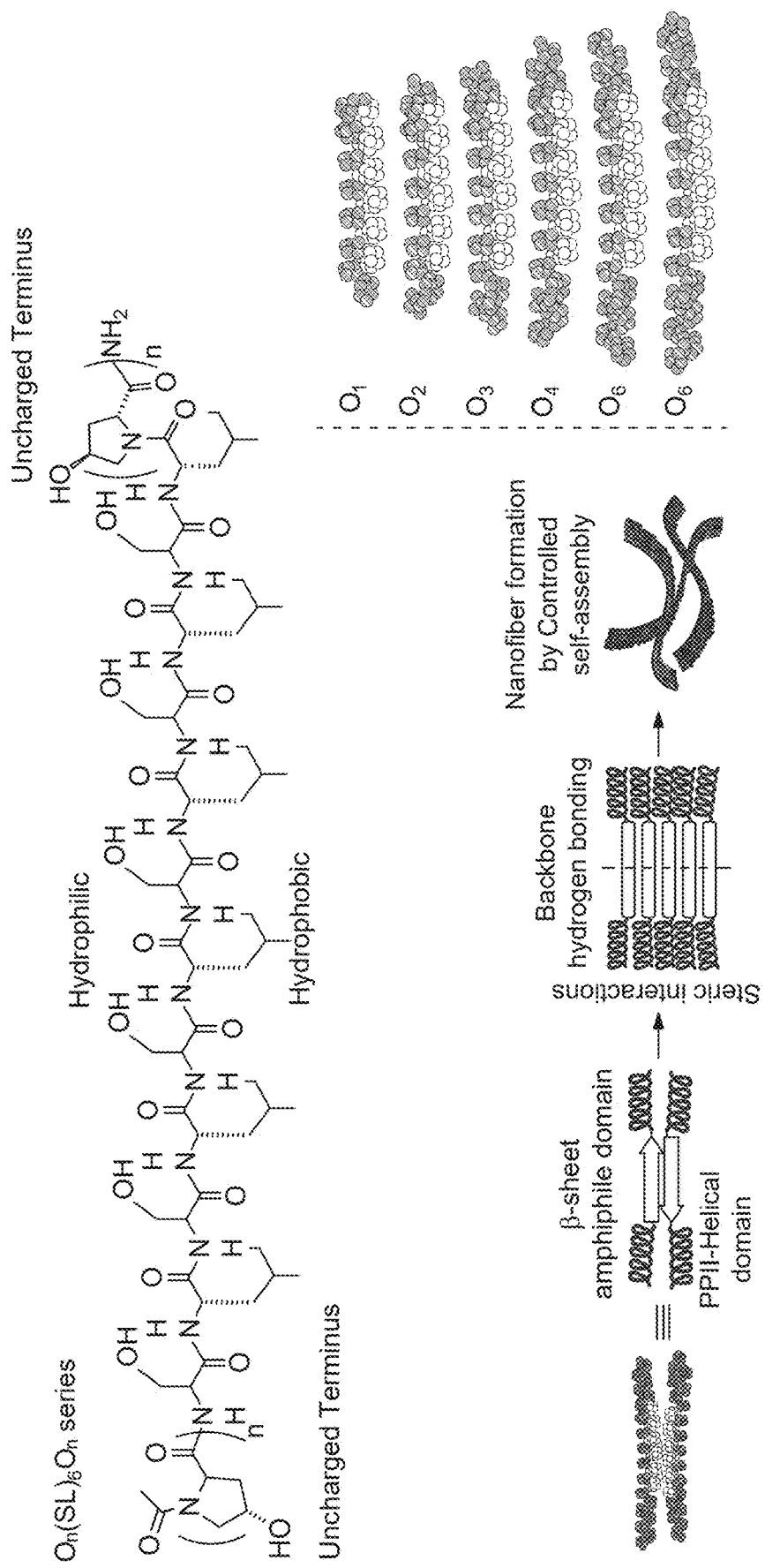
FIG. 1. Rational design of $O_n(SL)_6O_n$ peptide series. 4-Hydroxyproline (O) domains of variable length are incorporated into the N and C termini to create a bulky non-ionic domain. In solution, the amphiphilic domain has an antiparallel β-sheet conformation and assembles by H-bonding between peptide backbones. The non-ionic domain provokes steric interactions that frustrate the infinite aggregation of the MDPs forming nanofibers.

A simple and effective method to preserve quiescent stem cells is necessary to allow the use of these cells for different medical applications. The methods provided herein will facilitate the storage and availability of stem cells (e.g., hematopoietic stem cells, mesenchymal stem cells, human embryonic stem cells, induced-pluripotent stem cells) for long-term use, promote the development of cell banks, and allow for the performance of quality and safety testing, cell transportation, and processing.

The self-assembly of multidomain peptides need not involve the use of charged amino acids. Uncharged domains of oligo-hydroxyproline at the peptide termini form bulky helical structures that create molecular frustration between the β-sheet self-assembling domain and terminal steric interactions. These steric interactions from the hydroxyproline domains affect peptide solubility, aggregation, and nanofiber structure. While all peptides in the $O_n(SL)_6O_n$ peptide series (n=1-6) formed nanofibers, only $O_5(SL)_6O_5$ was able to form a hydrogel. This nanostructured hydrogel shows promising properties for biomedical applications, including rapid shear recovery and support for cell viability. It also appears to induce a quiescent state in cells over time, a property that may be desirable for cell preservation. This compliant hydrogel is promising as a cell preservation method, where the cells can be 3D encapsulated in this matrix with the required trophic support and stored for longer times. The cells can be released from the nanofibrous material by simply dispersing in media, recovering, and using for their final purpose. When implanted in vivo, the hydrogel is infiltrated by macrophages without evidence of eliciting an adverse inflammatory response and the implant is degraded over time. This work establishes the creation of a neutral biocompatible hydrogel and extends the scope of peptide-based self-assembling materials to encompass positive, negative, and neutral nanofiber chemistries for diverse biomaterial designs.

I. SELF-ASSEMBLING PEPTIDE HYDROGELS

Self-assembling peptides have been extensively studied because of their relationship to protein folding and assembly. These peptides can be designed to spontaneously self-assemble into fibrous nanomaterials that have a chemical composition and nanostructure that is readily interfaced with living systems and possess material properties that mimic the extracellular matrix (Lutolf & Hubbell, 2005). The resulting bio-interactive nature of these supramolecular materials is useful in biomedical applications, such as controlled drug and protein delivery, cell encapsulation, and tissue regeneration (Webber et al., 2015; Rad-Malekshahi et al., 2016; Leach et al., 2018). Several peptide designs have been created to self-assemble into nanoribbons, monolayers or nanofibers, which utilize amphiphilic and ionic domains to govern their supramolecular structure (Aggeli et al., 2003; Powers et al., 2002; Holmes et al., 2000; Cormier et al., 2013; Pochan et al., 2003; Hargerink et al., 2001).

Generally, self-assembling peptide design has required the incorporation of charged amino acids into the peptide sequence as a mechanism to control assembly and material properties by stimuli such as pH and ionic strength (Chockalingam et al., 2007; Micklitsch et al., 2011; Schneider et al., 2002). However, it is known that biological responses and cell behavior highly depend on the chemistry and charge of the interacting materials. For example, poly-lysine is commonly used for cell attachment and proliferation in culture techniques (Mazie et al., 1975; Blau, 2013), but this and many other cationic polymers show an inherent concentration-dependent cytotoxicity (Fischer et al., 2003; Kadlecova et al., 2012). On the other hand, neutral polymers, such as PEG, are inert, biocompatible, and non-immunogenic and have been used in countless studies to bestow these "stealth" properties on other materials (Zhu, 2010; Meyers & Grinstaff, 2012; Li et al., 2015). Neutral, non-ionic peptides tend to have poor solubility and aggregate or precipitate in aqueous solutions. This makes controlling the formation of finite supramolecular structures derived from these molecules challenging. Previously, steric interactions and size mismatch have been used to regulate the self-assembly of polymeric mushroom-shaped nanostructures (Stupp et al., 1997). Nevertheless, the field is limited by its ability to explore biological responses to only positively or negatively charged self-assembling peptide hydrogels because strategies to control peptide self-assembly through uncharged residues are limited.

Three-dimensional cell encapsulation in hydrogels have been use as a culture method, where cells have the support and biological cues to grow and proliferate in the material scaffold. These hydrogels are designed to promote cell attachment, growth and proliferation, while the hydrogel is being degraded over time. However, for stem cell preservation it is required to maintain the cell quiescence and avoid any potential differentiation until the cells are required. The use of hydrogels for stem cell preservation would provide a simple and less harmful method for cell storage. For that purpose, the material should not promote cell attachment or exogenous cues for the cells to proliferate, it should induce and maintain the quiescence state of stem cells, while still protecting cell viability for long periods of time.

Herein, steric frustration was used as a controlling mechanism for the solubility and self-assembly of neutral peptides. A series of peptides were designed to determine if self-assembly could be mediated by the steric impediment created by neutral hydroxyproline domains, eliminating the need for high charge. The absence of charged groups allowed the assembly and structure of the peptide to remain largely independent of pH and ionic strength. Peptide solubility and nanofiber length increased with a higher number of hydroxyproline residues giving $O_5(SL)_6O_5$ the optimal properties for self-assembly and hydrogelation. In vitro this hydrogel supports cell viability, while in vivo it is infiltrated with cells and easily degraded over time without promoting a strong inflammatory response. This neutral self-assembling peptide hydrogel shows promising properties for biomedical and cell preservation applications and expands the scope of available self-assembling peptide nanostructured materials that may be studied for applications in biology and medicine.

The present neutral, self-assembling multidomain peptide (NMDP) was designed to form a cytocompatible hydrogel material at physiological pH upon ultrasonication treatment. Gelation is independent of the presence of ions and pH variations, making this material robust and simple to use for cell culture. The NMDP hydrogel's viscoelastic properties, storage modulus (23.3±8.7 Pa), and loss modulus (1.7±0.5 Pa) demonstrate that this peptide forms a self-supporting compliant flexible gel, which can be easily pipetted or injected because of its shear thinning and shear recovery characteristics. The NMDP hydrogel exhibits a liquid behavior when high strain is applied, while having a very rapid recovery of approximately 92% of its initial storage modulus 1 minute after the strain is released.

The production of the present NMDP can follow these steps: Step 1: The peptide is synthesized using solid-phase peptide synthesis and FMOC strategy. The N-termini are acetylated before cleavage with TFA and scavengers. TFA is removed by rotary evaporation and solid peptide is recovered by trituration with diethyl ether. The NMDP is dialyzed against MQ $H_2O$ in 100-500 Da, pH adjusted to 7.2-7.4, sterile filtered, lyophilized, and stored at −20° C.

Step 2: Peptide solution of NMDP is prepared at 1% by weight in 149 mM sucrose and 0.5×HBSS. Then, the peptide solution is sonicated using a Microson Ultrasonic Cell Disruptor with a 2 mm microprobe at room temperature for 1 or 10 cycles, where each cycle consisted of 10 pulses and 1 min relaxation time between cycles. Sonication must be done before any cells are mixed. NMDP forms a compliant material that must be handled with more precautions. Changes of preservation media or buffer must be done with careful pipetting, otherwise there would be cell and material losses.

Step 3: Cells are isolated and incubated at 37° C. and 5% $CO_2$ before encapsulation. Cells are centrifuged for 6 min at 1600 rpm, then the cell pellet is dispersed in HBSS, counted and adjusted to the required concentration. The neutral hydrogel is prepared by sonication, as previously described, using only 90% of the required 149 mM sucrose-0.5×HBSS to obtain a 1% by weight concentration, the remaining 10% was added as a cell suspension, mixed, and homogenized. Conditions for the cell medium may be optimized for each cell type.

NIH 3T3 fibroblasts were encapsulated in NMDP hydrogel and cultured for up to 5 days. To evaluate the cytocompatibility and cell behavior promoted by NDMP, a cell viability test was performed using Calcein AM and Ethidium homodimer-1. Fibroblasts encapsulated in the NMDP hydrogel showed good initial viability, which remained constant throughout the experiment. Despite high and consistent cell viability in NMDP over the course of this study, the encapsulated fibroblasts were not observed to proliferate. The cells did not spread and adhere to the material, instead they remained "balled up." The lack of attachment to the hydrogel and balled up morphology suggest that the NMDP has achieved a "stealth" behavior present in other neutral polymers, such as PEG. All these observations suggest that fibroblasts cultured in NMDP are in a quiescent state. The ability of NMDP hydrogel to keep cells alive without proliferation is a promising result with potential applications for the use of this material in cell preservation.

The use of this novel NMDP for cell preservation avoids the use of exogenous factors to promote cell quiescence and the harsh conditions required for cryopreservation and freeze-thaw processes. The chemical design and viscoelastic properties of this neutral self-assembling peptide hydrogel provides a favorable environment for the cells to go into an inactive state while maintaining their viability and phenotype. The cells can be easily released from the hydrogel by simple disturbing the peptide matrix and resuspending the cells in media or buffer.

The peptides of the present disclosure can be lyophilized and dissolved in, for example, an appropriate concentration of sucrose solution or in deionized water. In one embodiment, the peptides can be provided in a 1-300 mM sucrose solution. The peptide concentration in the solution may be from about 0.1 mg/ml to about 100 mg/ml, from about 1 mg/ml to about 90 mg/ml, from about 10 mg/ml to about 80 mg/ml, from about 20 mg/ml to about 70 mg/ml, from about 30 mg/ml to about 60 mg/ml, from about 40 mg/ml to about 50 mg/ml, and any concentration therebetween.

II. PHARMACEUTICAL FORMULATIONS

The provided neutral multidomain peptides can be combined with a pharmaceutically acceptable carrier or vehicle for administration to human or animal subjects. In some embodiments, more than one multidomain peptide or peptide analog can be combined to form a single preparation. The multidomain peptides or peptide analogs can be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and nonaqueous sterile injection solutions which may contain anti-oxidants, buffers, bacteriostats and solutes; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition.

In certain, embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The pharmaceutical compositions provided herein may be administered through different routes, such as parenteral, intraperitoneal, intramuscular, subcutaneous, and intratumoral. It may be desirable to administer the pharmaceutical compositions locally to the area in need of treatment. This may be achieved by, for example, and not by way of limitation, local or regional infusion or perfusion during surgery, injection, or implant. In one embodiment, administration can be by direct injection at the site (or former site) of a tissue that is to be treated.

The amount of the pharmaceutical compositions that will be effective depends on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each subject's circumstances.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the subject undergoing therapy.

The pharmaceutical compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. The volume of administration will vary depending on the route of administration. Those of ordinary skill in the art will know appropriate volumes for different routes of administration.

III. METHODS OF TREATMENT

The present invention provides methods of treating a patient with neutral multidomain peptide hydrogels as provided herein.

The term "subject" or "patient" as used herein refers to any individual to which the subject methods are performed. Generally, the patient is human, although as will be appreciated by those in the art, the patient may be an animal Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

"Treatment" and "treating" refer to administration or application of a therapeutic agent to a subject or performance of a procedure or modality on a subject for the purpose of obtaining a therapeutic benefit of a disease or health-related condition.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease.

Likewise, an effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse.

For the treatment of disease, the appropriate dosage of a therapeutic composition will depend on the type of disease to be treated, as defined above, the severity and course of the disease, previous therapy, the patient's clinical history and response to the agent, and the discretion of the physician. The agent may be suitably administered to the patient at one time or over a series of treatments.

IV. KITS

Kits are envisioned containing peptides or hydrogels of the present invention. The kit may comprise reagents required for the formation of or the delivery of the hydrogel. The kit may also comprise a suitable container means, which is a container that will not react with components of the kit, such as an eppendorf tube, a syringe, a bottle, or a tube. The container may be made from sterilizable materials such as plastic or glass. The kit may further include an instruction sheet that outlines the procedural steps of the methods, such as the same procedures as described herein or are otherwise known to those of ordinary skill.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Figure 6:
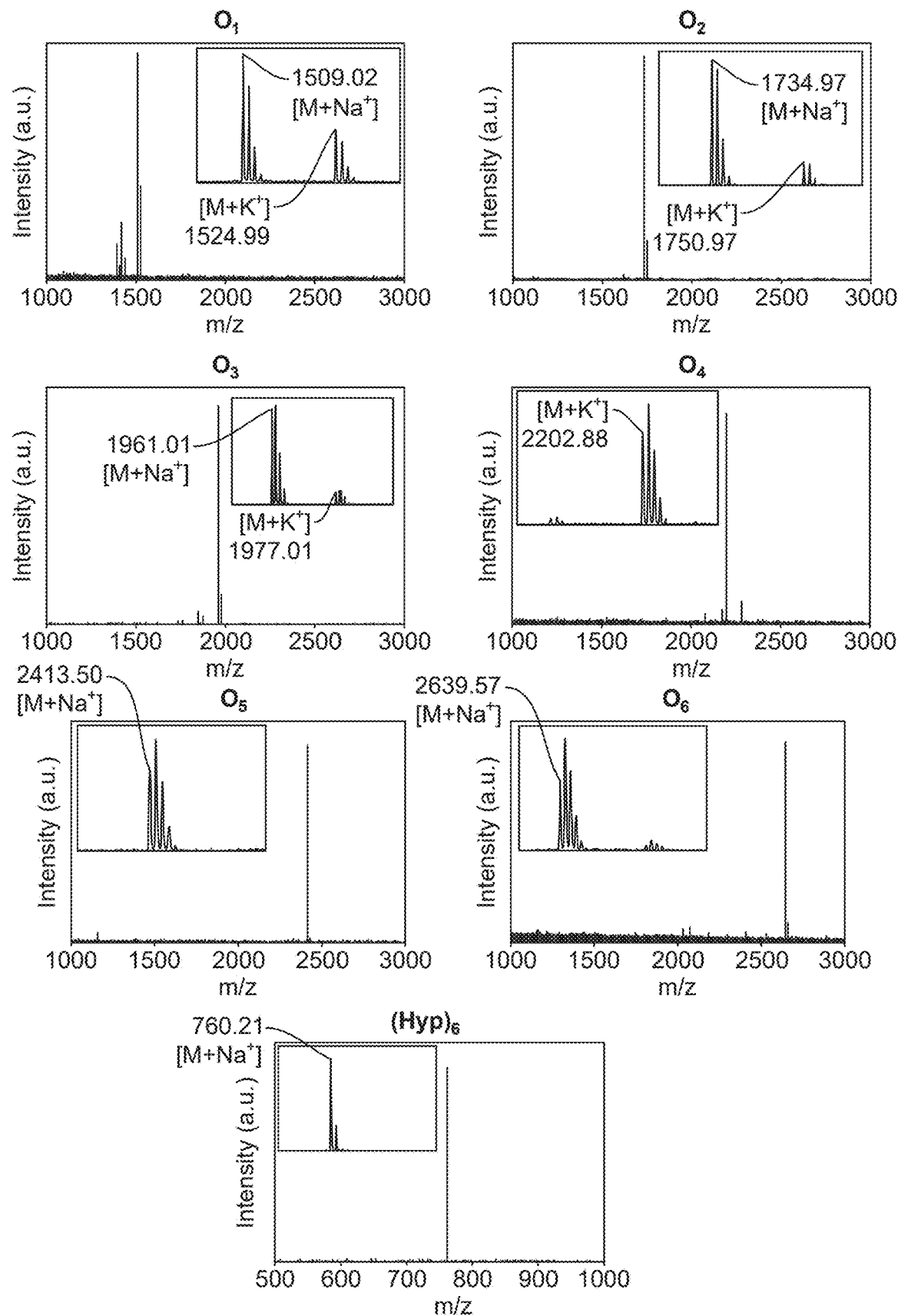
FIG. 6. MALDI TOF MS of $O_6(SL)_6O_n$ series.

Peptide synthesis. All peptides were synthesized using solid-phase peptide synthesis according to the methodology previously reported (Aulisa et al., 2009). Briefly, a semi-manual synthesis was accomplish using an Apex Focus XC (Aapptec) synthesizer for mixing, solvent addition, and wash steps. Low-loading Rink Amide MBHA resin (0.32 mmol/g) was used, and the N-termini were acetylated before cleavage with TFA and scavengers. TFA was removed by rotary evaporation and solid peptide was recovered by trituration with diethyl ether. $O_1$ and $O_2$ were washed with Milli-Q deionized $H_2O$ because of their poor solubility, while $O_3$-$O_6$ were dialyzed against MQ $H_2O$ for 3-4 days in 100-500 Da or 1000 Da MWCO dialysis tubing (Spectra/Por, Spectrum Laboratories Inc., Rancho Dominguez, CA). Peptide solutions were adjusted to pH 7.2, sterile filtered when solubility allowed, frozen, lyophilized, and stored at −20° C. All peptides were characterized using Autoflex MALDI-TOF MS (Bruker Instruments, Billerica, MA) to confirm purity and correct mass (FIG. 6). Samples for MALDI-TOF MS characterization were prepared as follows: peptides were dissolve in TFE:$H_2O$:MeOH (1:1:0.2) acidified with 0.05% trifluoracetic acid (TFA). The peptide solution was mixed with α-CHCA matrix solution (in 50% acetonitrile) in a 1 to 1 ratio while being spotted on a ground steel MALDI target plate. Droplets were allowed to dry before the analysis.

Circular Dichroism (CD) spectroscopy. For secondary structure characterization, peptide solutions of 1% by weight (molar concentration is included in Table 2) were prepared in 2,2,2-trifluoroethanol (TFE, Sigma Aldrich, St. Louis, MO). CD spectra acquisition was performed in a CD Jasco J-810 spectropolarimeter (Jasco Inc., Easton, MD) using a 0.01 mm cuvette. Data were collected at room temperature from 180 to 250 nm at a speed of 50 nm/min, with a 0.1 nm data pitch and the spectra were averaged over 5 scans. To study the hydrogelation of $O_5$, 1% by weight peptide solutions were made in 149 mM sucrose solution in 0.5× Hank's Balanced Salt Solution (HBSS, Life Technologies) and analyzed as previously described.

Figure 7:
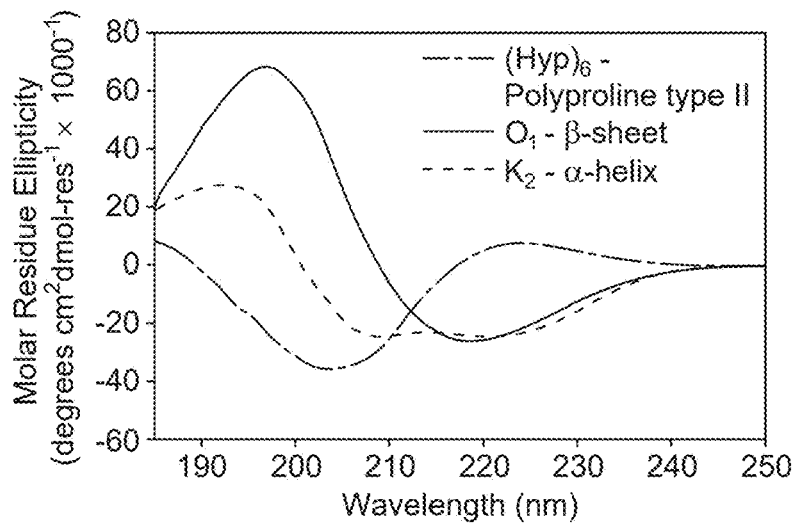
FIG. 7. Basis spectra for CD spectroscopy data fitting in a) 2,2,2-trifluoroethanol (TFE) 1 wt. % solutions. At 200 nm, the top line is $O_1$-β-sheet, the middle line is $K_2$-α-helix, and the bottom line is (Hyp)$_6$-Polyproline type II.

To estimate the secondary structure of O peptide series, data fitting using the least square linear method was performed in MATLAB (Mathworks, Natick, MA). $(Hyp)_6$, $O_1(SL)_6O_1$ and $K_2(SL)_6K_2$ were used as basis spectra for polyproline type II, β-sheet and α-helix, respectively (FIG. 7). As has been demonstrated in other systems, TFE promotes the formation of α-helical structures (Myers et al., 1998); therefore, α-helix was considered as a possible structure to achieve a better estimation.

Attenuated Total Reflectance Fourier Transform Infrared Spectroscopy (ATR-FTIR). Peptide samples (10 µL of 1% by weight peptide solution) were dried under nitrogen flow on a Golden Gate diamond window of an ATR stage or on a glass slide. IR spectra were collected on a Jasco FT/IR-660 plus spectrometer (Jasco Inc., Easton, MD) and a Nicolet iS5 FT/IR spectrometer (Thermo Scientific, Waltham, MA) at 1 $cm^{-1}$ resolution with 64 scans accumulation, and the background was subtracted, and vapor reduction was applied to minimize the contribution of water in the resulting spectra. Spectragryph—optical spectroscopy software was used for data processing and normalization (Menges, 2017).

Transmission Electron Microscopy (TEM). For TEM, 1% by weight peptide solutions in TFE or Milli-Q $H_2O$ were diluted to concentrations ranging from 0.1% by weight to 0.01% by weight with Milli-Q water. All samples were prepared via negative staining on Quantifoil R1.2/1.3 holey carbon films on copper mesh grids. Each peptide was spotted and allowed to adsorb for 1 min before excess peptide was blotted. A 2 wt. % phosphotungstic acid (PTA) solution in Milli-Q water was prepared at pH 7 and sterile filtered. The sample grids were negative stained for 5 min in PTA. Excess PTA was wicked off the grids before the samples were dried and imaged at 120 kV and 40K magnification using a JEOL 2010 TEM microscope (JEOL USA Inc., Peabody, MA).

Hydrogel Formation. Peptide solutions of $O_5$ were prepared at 1% by weight (4.2 mM) in 149 mM sucrose and 0.5×HBSS. This buffer system was chosen to be consistent with prior MDP experiments and find optimum gelling conditions for future in vivo and in vitro work. Peptide solutions were sonicated using a Microson Ultrasonic Cell Disruptor with a 2 mm microprobe. The instrument frequency was 22.5 kHz and a power output up to 10 watts (RMS) was used. Solutions were sonicated at room temperature for 1 or 10 cycles, where each cycle consisted of 10 pulses and 1 min relaxation time between cycles. For the study of hydrogelation of $O_5$, $K_2$ and $E_2$ at different pH values and ionic strength, 1% by weight peptide solutions were prepared in deionized water, PBS, or HBSS. pH was adjusted using HCl or NaOH 0.1 M solutions.

Oscillatory Rheology. Rheological properties of $O_5$ hydrogel were analyzed by oscillatory rheology using a TA Instruments AR-G2 rheometer (TA Instruments, New Castle, DE). Hydrogels were prepared 24 h before the analysis as described above. 150 µL of 1% by weight peptide hydrogels were transferred from a cut syringe onto the rheometer stage equipped with a 12 mm stainless-steel parallel plate set to a 1000 µm gap height. The following program was used to monitor the storage modulus (G') and loss modulus (G") under various conditions as has been previously published (Li et al., 2017). Strain sweep analysis was performed using an applied strain of 0.01%-200% at a frequency of 1 rad/s. Frequency sweep analysis was performed under 1% strain at 0.1-100 rad/s. Shear recovery analysis was performed by subjecting the peptide sample to 1% strain for 20 min, then 200% for 1 min, and finally 1% for 20 min, allowing for disruption of the hydrogel and monitoring of G' and G" recovery.

Scanning Electron Microscopy (SEM). For SEM characterization, 1% by weight peptide hydrogel was prepared as previously described. Hydrogel was dehydrated with a series of ethanol from 30% to 100% and the ethanol was removed by critical point drying using an EMS 850 critical point dryer (Electron Microscopy Sciences, Hatfield, PA). Dried samples were mounted into SEM pucks with conductive carbon tape and coated with 4 nm of gold using a Denton Desk V Sputter system (Denton Vacuum, Moorestown, NJ). Samples were imaged using a JEOL 6500F Scanning Electron Microscope (JEOL, USA Inc., Peabody, MA).

Cytocompatibility and cell viability studies. All cell culture materials, not otherwise specified, were purchased from Gibco, Life Technologies. NIH-3T3 fibroblast cells were cultured in Dulbecco's Modified Eagle Medium (DMEM) supplemented with 10% Fetal Bovine Serum (FBS), 2% L-glutamine (200 mM), 1% sodium pyruvate (100 mM), and 1% pen-strep solution (5000 units/mL of penicillin and 5 mg/mL of streptomycin, Sigma-Aldrich, St. Louis, MO). Cells were maintained at 37° C. and 5% $CO_2$ with humidity and split when reaching 80%-90% confluency by treatment with 0.25% trypsin-EDTA and neutralization with complete media. Cells were centrifuged for 6 min at 1600 rpm, then the cell pellet was dispersed in HBSS, counted and adjusted to the required concentration. 3D cell culture in $K_2$ hydrogel was achieved by mixing a 2% by weight peptide stock solution in 298 mM sucrose with a cell suspension of $2\times10^6$ cells/mL in HBSS. The final concentration was 1% by weight $K_2$ hydrogel in 149 mM sucrose and 0.5×HBSS with $1\times10^6$ cells/mL. For $O_5$ peptide, hydrogel was prepared by sonication using only 90% of the required 149 mM sucrose-0.5×HBSS to obtain a 1% by weight concentration, the remaining 10% was added as a cell suspension, and mixed by pipetting into the gel to obtain a final concentration of $1\times10^6$ cells/mL evenly distributed though the volume of the hydrogel. 70 µL of seeded hydrogels were cultured in a Lab-Tek 16-well glass chamber (0.4 $mm^2$, Thermo Fisher, Rochester, NY) with 200 µL of medium and fed every 2 days by replacing 100 µL with fresh media. Cell viability was analyzed using a live/dead viability kit (Invitrogen, Thermo Fisher, Carlsbad, CA). At specific time points, the medium was removed, and gels were rinsed with 1×PBS, then 100 µL of staining solution containing 2 µM Calcein AM and 4 µM Ethidium homodimer-1 in DPBS were added. Cells were incubated from 15 to 30 min and imaged using a Nikon A1 Rsi fluorescent confocal microscope (Nikon Instruments, Tokyo, Japan). Three z-stack images of 100 µm deep per sample were taken at 20× using a 488 nm green channel and 561 nm red channel lasers. Images were processed with NIS Element and live/dead cell counting was performed on Imaris 3D/4D Image Processing software (Bitplane, Concord, MA).

To evaluate the cell morphology, hydrogels were rinsed with PBS and fixed with 10% buffered formalin for 30 min Cells were treated with 0.5% Triton X for 10 min and 100 mM glycine for 10 min, followed by 10% Bovine Serum Albumin (BSA) in HBSS block solution. Then cells were stained for filamentous actin with Alexa Fluor® 488-Phalloidin and for the nuclei with ProLong® Gold Antifade DAPI mounting media. Cell in the hydrogels were analyzed by confocal microscopy using a 40× water objective and processed as described.

In vivo compatibility studies. All experimental procedures were approved by the Rice University Institutional Animal Care and Use Committee (IACUC) and performed according to the Animal Welfare Act and NIH guidelines. Female C57BL/6 mice from 8 to 12 weeks were purchased from Charles River (Wilmington, MA). Mice were injected with 4 implants of 100 µL 1% by weight $O_5$ hydrogel in the dorsal subcutaneous space using a 26-gauge needle. At days 3, 7, and 14 mice were euthanized, and implants were extracted, fixed with 10% neutral buffered formalin and processed into paraffin blocks. Tissue was sectioned at 5 μm thickness and stained with hematoxylin and eosin, and Masson's trichome under standard procedures. For fluorescent immunostaining, tissue sections were deparaffinized, hydrated and antigens were retrieved by boiling in sodium citrate buffer (10 mM sodium citrate, 0.05% Tween 20 at pH 6.0). Tissues were permeabilized with 0.5% Triton X and blocked with 1% BSA in PBS for 30 min. Tissues were incubated overnight at 4° C. with rat anti-Mouse F4/80 monoclonal antibody (1:50, clone BM8, eBioscience™, Cat #14-4801-82). Then, samples were incubated for 1 hour with goat anti-rat AlexaFluor® 568 (1:500, Invitrogen), followed by mounting with ProLong® Gold Antifade reagent with DAPI. Tissue slides were analyzed by confocal fluorescent microscopy.

Example 1—$O_n(SL)_6O_n$ Series Peptides

Previously, a class of self-assembling peptides, called Multidomain Peptides (MDPs), has been studied (Dong et al., 2007). These peptides are designed with an ABA motif, where the B domain alternates hydrophilic and hydrophobic amino acids while the A domain contains charged residues. The balance between charge repulsion at the ends of the peptide and stabilizing hydrogen bonding and hydrophobic packing in the core controls the extent of self-assembly. In aqueous solution, the peptides typically adopt an antiparallel sheet conformation and assemble into nanofibers driven by the hydrophobic effect and hydrogen bond formation between backbone amides. Fiber length and stability are modulated by pH or the addition of multivalent ions, which screen the electrostatic repulsion and shift the balance of supramolecular forces towards assembly of nanofibers. Upon achieving sufficient length, these nanofibers entangle and form a viscoelastic hydrogel (Dong et al., 2007; Aulisa et al., 2009; Bakota et al., 2013; Moore & Hartgerink, 2017). Following a similar rationale, the neutral MDP design presented here is composed of the same amphiphilic core with alternating hydrophilic and hydrophobic amino acids comprised by the twelve amino acid sequence $(SL)_6$. This domain drives intermolecular β-sheet hydrogen bonding and hydrophobic packing. However, this domain by itself yields insoluble nanofibers which precipitate in solution. Instead of using charged termini to improve solubility, the current design selects hydroxyproline (here abbreviated as O) as non-ionic termini. Hydroxyproline provides the necessary hydrophilicity with its hydroxyl side chain and, more importantly, cannot participate in the N—H backbone hydrogen bond donation required in the formation of β-sheets. Additionally, hydroxyproline repeats are predisposed to form polyproline type II (PPII) helices, which can provide a bulky terminus to establish molecular frustration by steric impediment to the growing peptide nanofibers. To study the effect of oligo-hydroxyproline on the self-assembly of nanofibers and subsequent hydrogelation, MDPs with a variable number of hydroxyproline residues, $O_n(SL)_6O_n$ where n=1-6, were designed and synthesized (FIG. 1, Table 2).

TABLE 2

$O_n(SL)_6O_n$ series and control peptides

| Name | SEQ ID NO: | Sequence | Mono-isotopic mass (Da) | Molecular weight (Da) | Molar conc. of 1 wt.% solutions (mM) |
|---|---|---|---|---|---|
| $O_1$ | 1 | Ac-OSLSLSLSLSLSLO-CONH$_2$ | 1485.83 | 1486.71 | 6.7 |
| $O_2$ | 2 | Ac-OOSLSLSLSLSLSLOO-CONH$_2$ | 1711.93 | 1712.94 | 5.8 |
| $O_3$ | 3 | Ac-OOOSLSLSLSLSLSLOOO-CONH$_2$ | 1938.04 | 1939.17 | 5.1 |
| $O_4$ | 4 | Ac-OOOOSLSLSLSLSLSLOOOO-CONH$_2$ | 2164.15 | 2165.41 | 4.6 |
| $O_5$ | 5 | Ac-OOOOOSLSLSLSLSLSLOOOOO-CONH$_2$ | 2390.25 | 2391.64 | 4.2 |
| $O_6$ | 6 | Ac-OOOOOOSLSLSLSLSLSLOOOOOO-CONH$_2$ | 2616.35 | 2617.87 | 3.8 |
| $K_2$ | 7 | Ac-KKSLSLSLSLSLSLKK-CONH$_2$ | 1772.10 | 1773.17 | 5.6 |
| $E_2$ | 8 | Ac-EESLSLSLSLSLSLEE-CONH$_2$ | 1775.89 | 1776.94 | 5.6 |
| $(Hyp)_6$ | 9 | Ac-OOOOOO-CONH$_2$ | 737.34 | 737.75 | 1.4 |

Figure 2A:
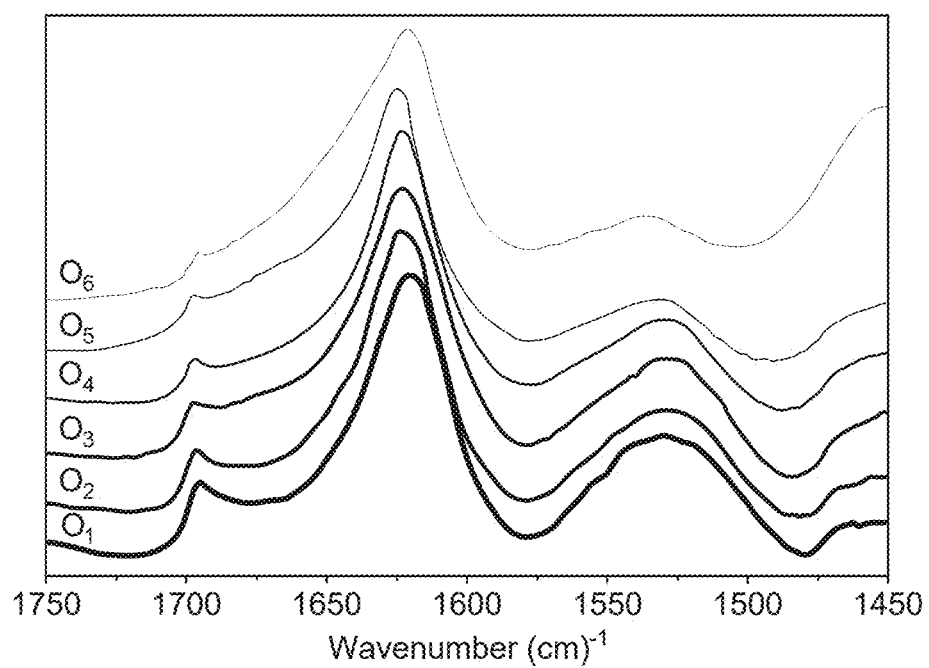
Figure 2B:
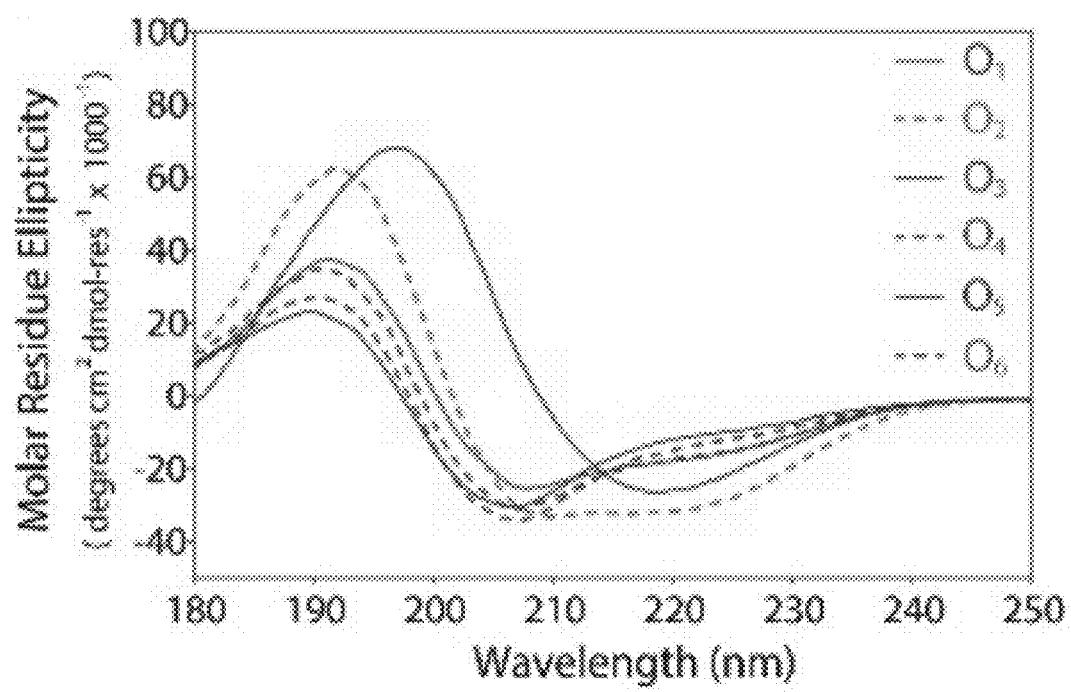

Example 2—Secondary Structure Characterization of $O_n(SL)_6O_n$ Series Peptides From the series of $O_6(SL)_6O_6$ peptide, $O_1$-$O_4$ were poorly soluble in water (<0.5 mg/mL) and resulted in the formation of a heterogeneous suspension. In contrast $O_5$ and $O_6$ were found to be soluble in water at 1 mg/mL. At 10 mg/mL, $O_5$ forms a hydrogel while $O_6$ is a viscous solution. The ATR-FTIR spectra (FIG. 2A) of the dried peptide films presented a peak between 1620-1630 $cm^{-1}$, which corresponds to the amide I band of a β-sheet conformation, and a weak peak around 1695 $cm^{-1}$ indicating an antiparallel component. These results indicate that the core β-sheet structure is not significantly disturbed by the oligo-hydroxyproline termini in the dried samples. Poor solubility of $O_1$-$O_4$ made the characterization across all peptides in uniform solvent challenging, therefore 2-2-2-trifluoroethanol (TFE) was often used as a solubilizing agent for sample preparation and characterization. Circular dichroism (CD) spectroscopy of peptide solutions in TFE (1% by weight, 7-4 mM) was performed (FIG. 2B). CD of $O_1$ corresponds to a canonical β-sheet structure, presenting minima at 218 nm and maxima at 197 nm. Peptides $O_2$ through $O_6$ display a combination of different secondary structures. However, increasing numbers of hydroxyproline residues resulted in a corresponding increased fraction of PPII secondary structure as determined using a least square linear fitting method (Tables 2 & 3). While the peptides also showed an α-helical component, this is due to the propensity of TFE to promote this conformation (Sonnichsen et al., 1992; Roccatano et al., 2002). Together the IR and CD suggests the secondary structure of this series of peptides is β-sheet in the amphiphilic (SL)$_6$ core while the $O_n$ termini in $O_2$-$O_6$ adopt a PPII helical structure. This PPII helix becomes large enough to mediate solubility at $O_5$ and $O_6$.

TABLE 3

Estimation of the secondary structure of O series peptides in TFE at 25° C. from circular dichroism data using the least square linear method

| Peptide | % PPII[a] | % β-sheet[a] | % α-helix[a] | nmrsd[b] | Predominant Structure |
|---|---|---|---|---|---|
| $O_1$ | 0 | 100 | 0 | 2.7 × 10$^{-15}$ | β-sheet |
| $O_2$ | 29.3 | 28.8 | 41.9 | 1.53 | α-helix |
| $O_3$ | 38.4 | 25.2 | 36.4 | 0.39 | PPII/α-helix |
| $O_4$ | 41.8 | 17 | 41.2 | 0.25 | PPII/α-helix |
| $O_5$ | 50 | 9.5 | 40.5 | 0.08 | PPII |
| $O_6$ | 48.5 | 11.4 | 40.2 | 0.05 | PPII |

Figure 8:
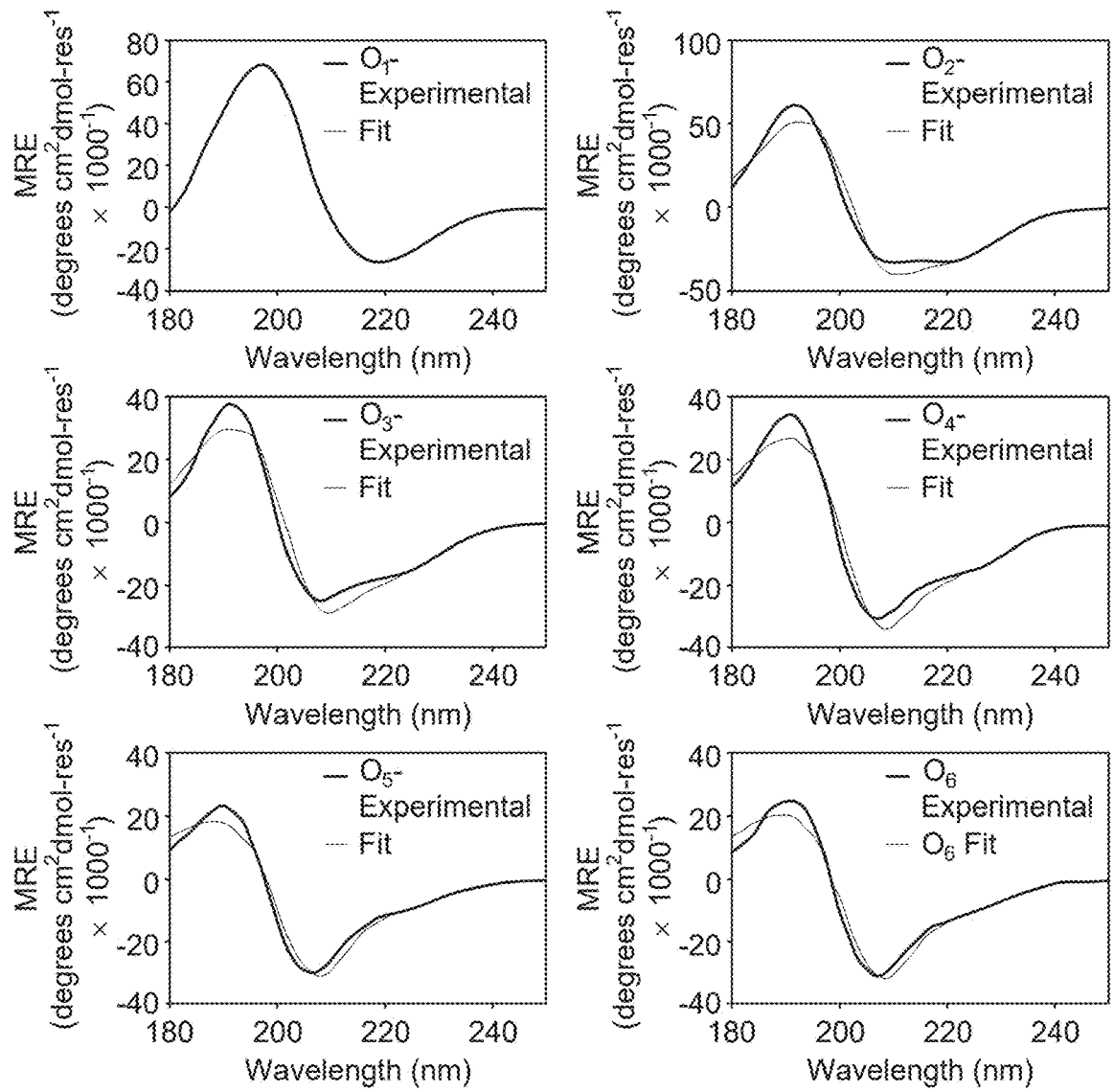
FIG. 8. Experimental and fit CD spectra of the O peptide series calculated by the least square linear method. At 210 nm, the top lines are Experimental and the bottom lines are Fit.

[a]Percentage of each structure was calculated from the regression estimator coefficients (SI Table 4, FIG. 8). Basis spectra for the determination of peptide secondary structure were: $O_1$ for β-sheet, (Hyp)$_6$ for polyproline type II, and $K_2$ for α-helix (FIG. 7).
[b]nmrsd is normalized root square deviation.

TABLE 4

Regression estimator coefficients of the analysis of peptide solutions in TFE by the least square linear method (β-sheet, PPII, α-helix)

| Peptide | β-sheet | PPII | α-helix | rms[a] | nmrsd[b] | Major contribution |
|---|---|---|---|---|---|---|
| $O_1$ | 1 | 0 | 0 | 1.04 × 10$^{-12}$ | 2.7 × 10$^{-15}$ | β-sheet |
| $O_2$ | 0.59 | 0.60 | 0.86 | 36.31 | 1.53 | α-helix |
| $O_3$ | 0.36 | 0.55 | 0.52 | 19.24 | 0.39 | α-helix - PPII |
| $O_4$ | 0.26 | 0.64 | 0.63 | 23.12 | 0.25 | PPII - α-helix |
| $O_6$ | 0.15 | 0.64 | 0.53 | 5.78 | 0.05 | PPII |

[a]rms: root mean square
[b]nmrsd: normalized root square deviation

Example 3—Nanostructure of $O_n$(SL)$_6$$O_n$ Series Peptides

Figure 3:
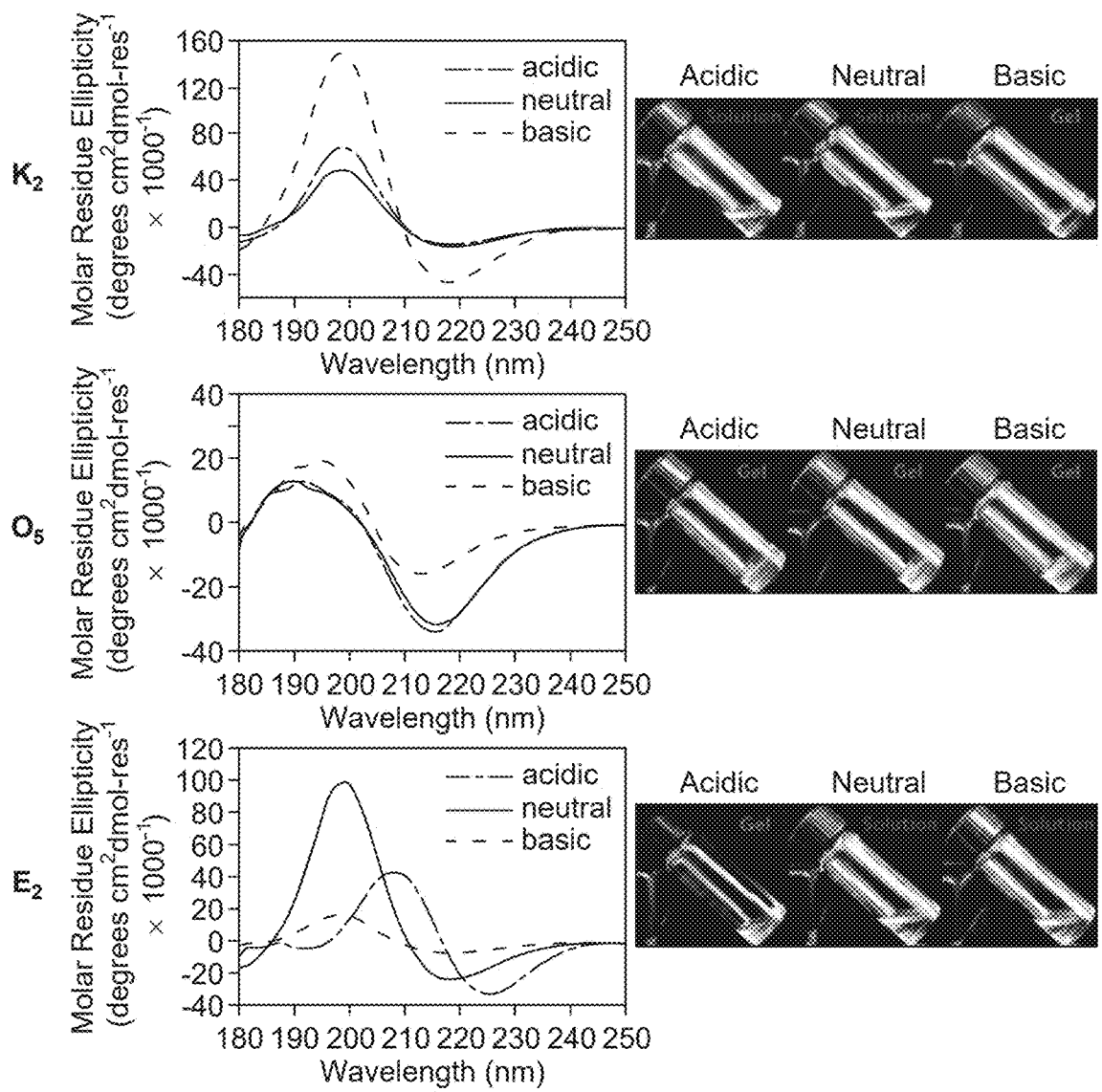
FIG. 3. $O_5(SL)_6O_5$ hydrogel properties are pH and ionic strength independent. CD spectra of the positively charged MDP, $K_2(SL)_6K_2$, neutral $O_5$ and negatively charged, $E_2(SL)_6E_2$ at different pH. $K_2$ and $E_2$ hydrogel formation is dependent on pH, whereas $O_5$ remains a hydrogel at acidic, neutral and basic pH. For $K_2$, at 200 nm, the top line is basic, the middle line is acidic, and the bottom line is neutral. For $O_5$, at 210 nm, the top line is basic, the middle line is neutral, and the bottom line is acidic. For $E_2$, at 190 nm, the top line is neutral, the middle line is basic, and the bottom line is acidic.
Figure 9:
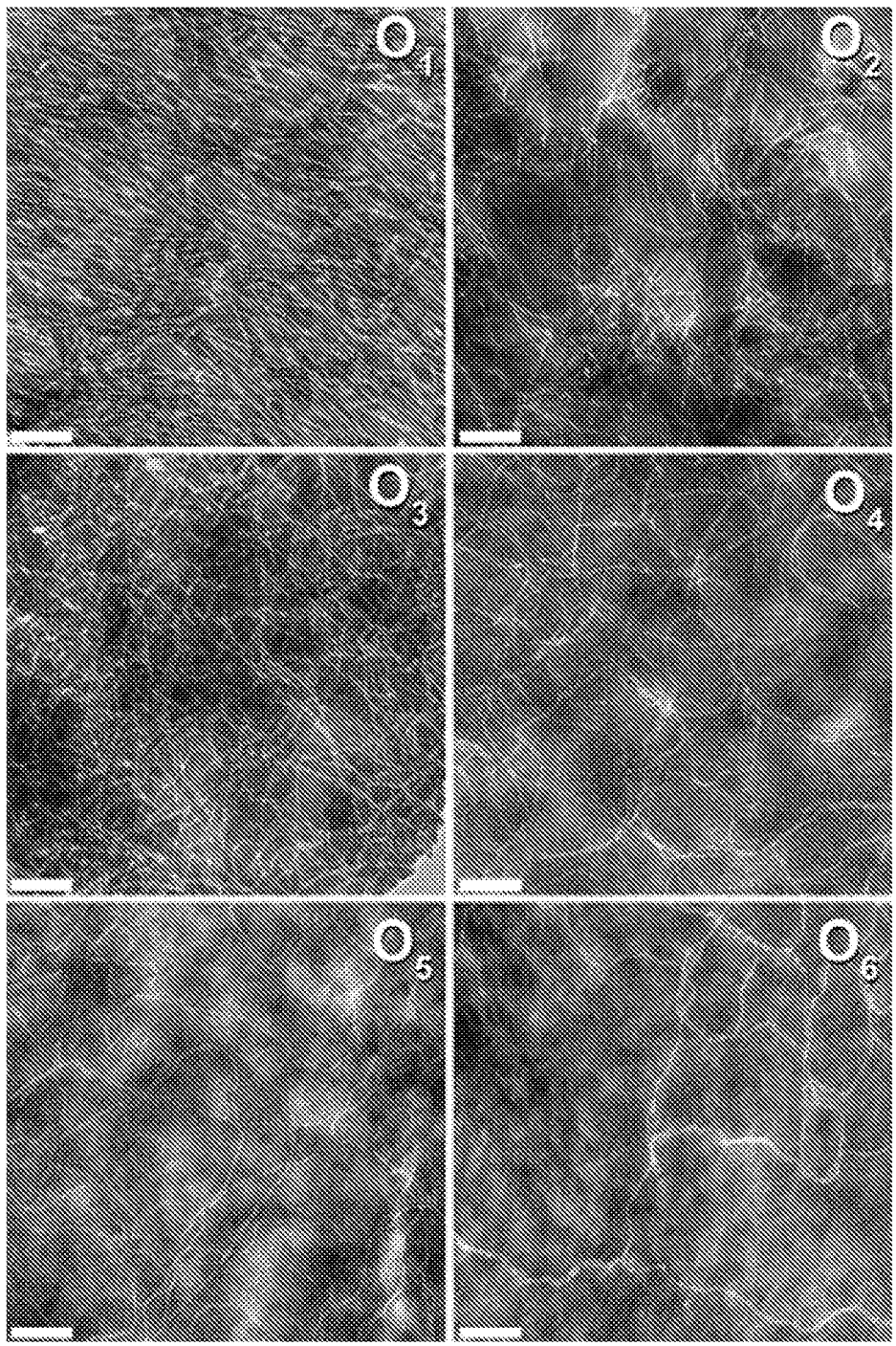
FIG. 9. Negative-stained TEM images of $O_n(SL)_6O_n$ dissolved initially in 2,2,2-trifluoroethanol (TFE) at 1 wt. % and diluted with water to final concentration. $O_1$ at 0.001 wt. %, $O_2$, $O_3$, $O_4$, $O_5$ and $O_6$ at 0.01 wt. %. Scale bar=100 nm.
Figure 10:
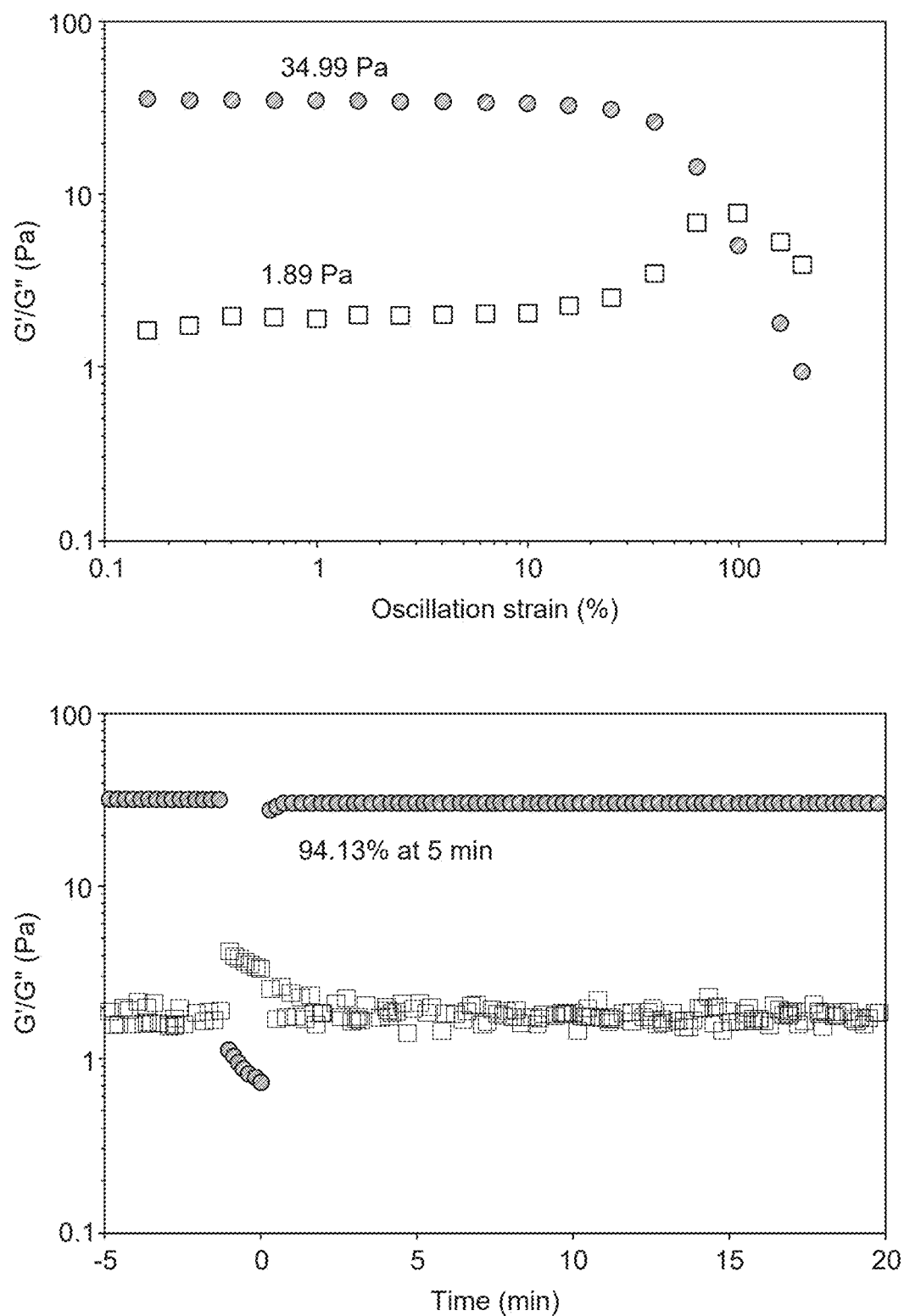
FIG. 10. Viscoelastic properties of $O_5(SL)_6O_5$ peptide hydrogel at 1 wt. % in PBS (5 mM phosphate and 150 mM NaCl).
Figure 11:
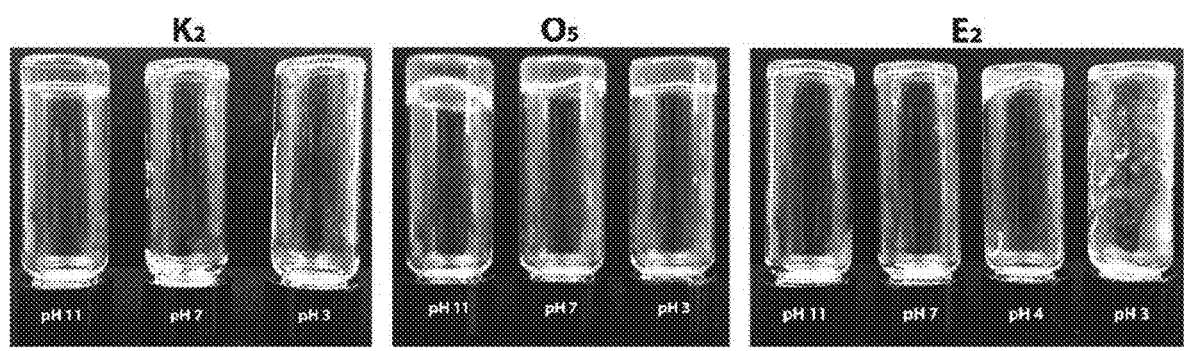
FIG. 11. Inverted-vial test of $K_2(SL)_6K_2$, $O_5(SL)_6O_5$ and $E_2(SL)_6E_2$ peptide solutions/hydrogel at acidic, neutral and basic pH. Positively charged MPD ($K_2$) forms a gel at pH 11, negatively charged MDP ($E_2$) forms a gel at acidic pH and undergoes phase separation. Neutral MDP ($O_5$) remains a hydrogel at all pH and without the presence of multivalent ions.

Negative-stain TEM was used to analyze the nanostructure of the $O_1$-$O_6$ peptide series. The very poor water solubility of $O_1$ and $O_2$ resulted in dense clusters of nanofibers along with amorphous aggregates in their TEM images with only rare areas being dispersed enough to see the underlying nanofibrous structure (FIG. 2C). However, the dispersion of the nanofibers increases with the number of hydroxyproline residues, improving their visualization. Also, the apparent fiber length increases with greater numbers of hydroxyproline residues. While fibers from $O_1$-$O_4$ appear mostly short and rigid, $O_5$ and $O_6$ nanofibers are significantly longer and display more curvature, suggesting a more flexible fiber. TEM was also performed on $O_1$-$O_6$, which had been initially dissolved in TFE to help disperse the assembled nanofibers and revealed similar trends to those formed only in water (FIG. 9). These data suggest that the increase in hydroxyproline residues and, therefore, PPII content in the peptide structure, modulate the solubility and nanostructure of the fibers by increasing both the hydrophilicity and steric frustration in the supramolecular assembly. Too short of an $O_n$ termini and the peptides assemble into short, rigid, low solubility fibers that form dense aggregates and precipitate. In contrast, too long of an $O_n$ termini and the peptide assembles into long, easily solubilized fibers, but with too few physical crosslinks to support gelation. Only $O_5$(SL)$_6$$O_5$ has the right balance of fiber length, rigidity, and solubility to form a hydrogel. This peptide remains a hydrogel over a wide pH range (3-11) as well as in deionized water (FIG. 3) and common buffers, such as phosphate-buffered saline (10 mM phosphate, 137 mM NaCl) (FIG. 10) and Hank's Balanced Salt Solution (HBSS). Similarly, the secondary structure as examined by CD has only minor changes under this range of conditions demonstrating the robustness of the neutral MDP approach. In contrast, charged MDPs, such as $K_2$(SL)$_6$$K_2$ and $E_2$(SL)$_6$$E_2$, have a strong dependence on pH and ionic strength with gels only forming at neutral pH or at elevated ionic strength (FIGS. 3 & 11), and significant changes to secondary structure are observed across these conditions that correlate to the ionization or shielding of their charged residues.

Example 4—Hydrogelation of $O_5$ Peptide

Figure 4A:
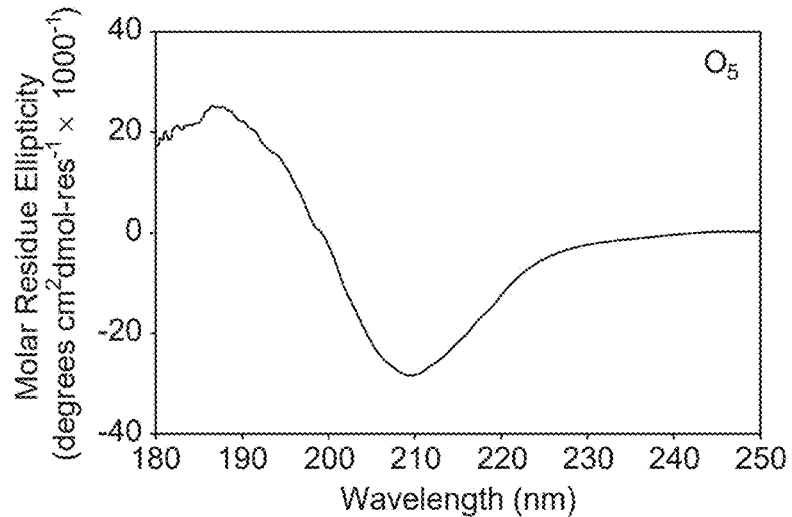
FIGS. 4A-D. $O_5(SL)_6O_5$ peptide solution forms a hydrogel upon treatment with ultrasonication.
Figure 4B:
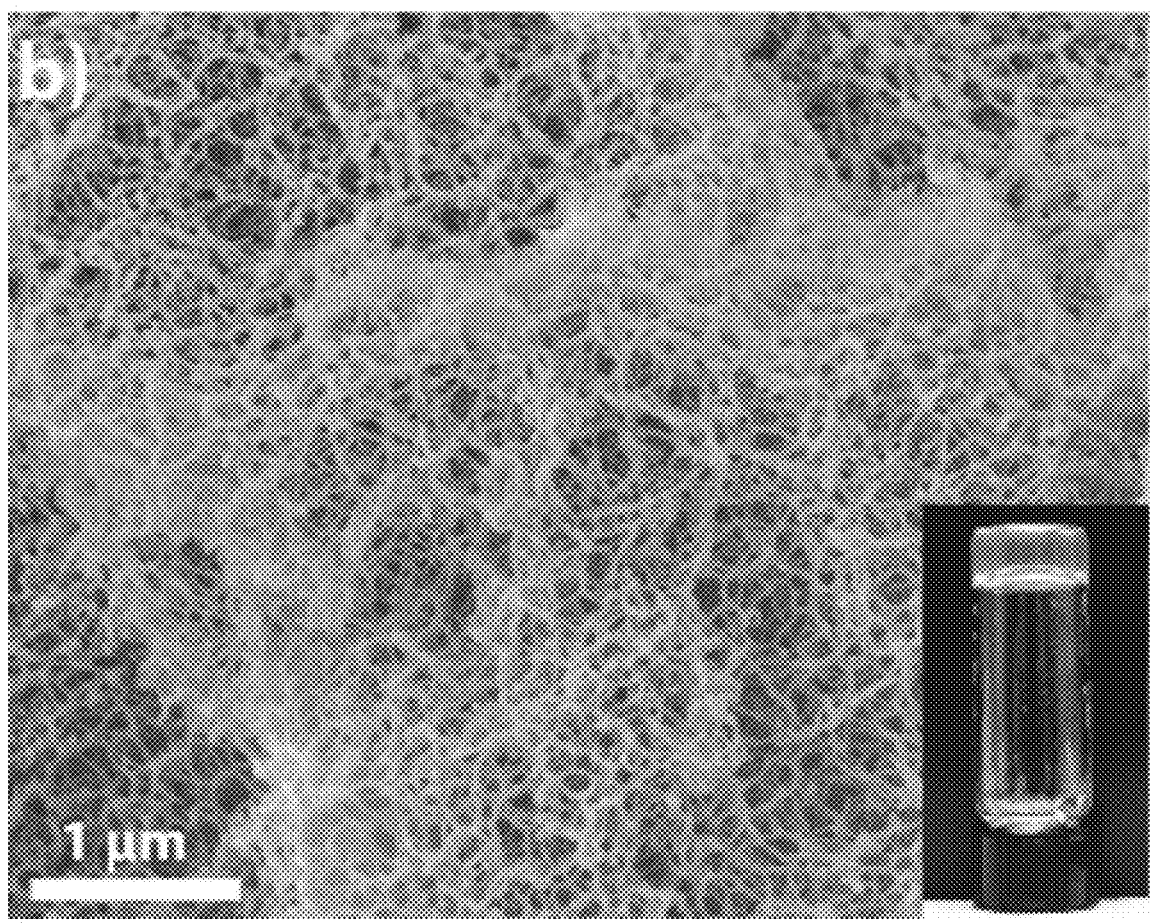
Figure 4C:
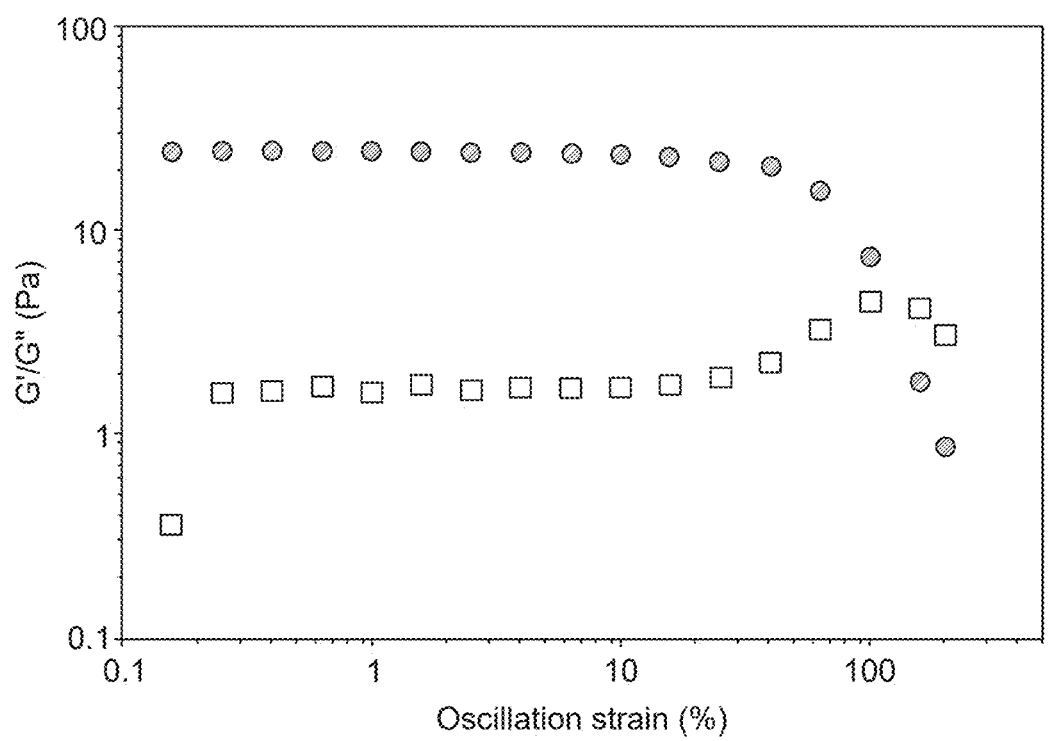
Figure 4D:
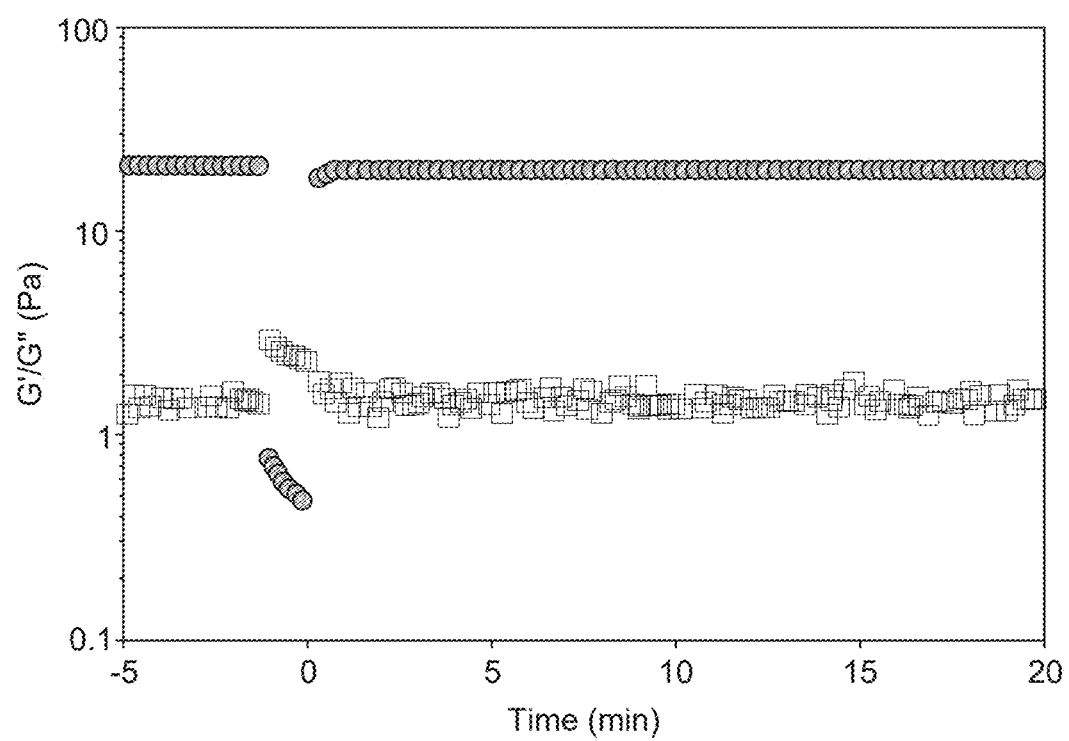
Figure 12:
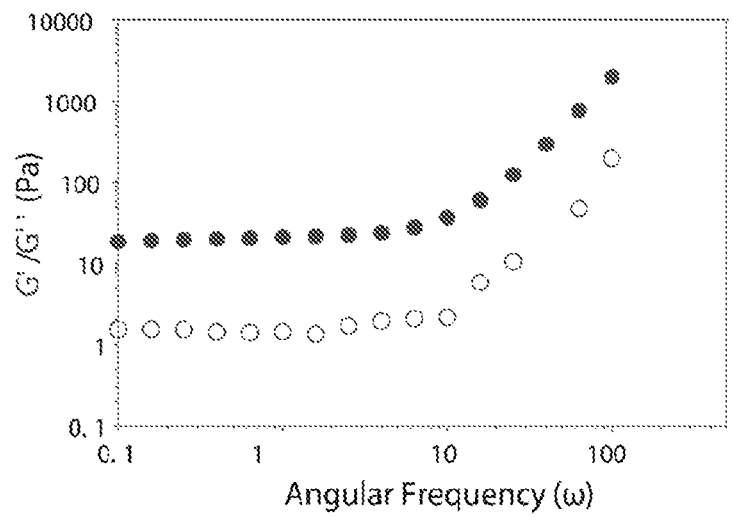
FIG. 12. Frequency sweep of $O_5(SL)_6O_5$ peptide hydrogel at 1 wt. % in 149 mM sucrose and 0.5×HBSS.

Hydrogel formation of previously designed MDPs is achieved by the addition of multivalent ions, such as phosphate, to induce gelation at neutral pH. This is a convenient media since these buffers are also required for most cell culture work. To assess the biological potential of the $O_n$ series of peptides, hydrogelation was tested in media that supports cell culture (1% by weight in 149 mM sucrose and 0.5×HBSS) and is commonly used to test charged MDPs, such as $K_2$(SL)$_6$$K_2$ and $E_2$(SL)$_6$$E_2$ (Moore & Hartgerink, 2017). Under these conditions, $O_5$ forms a self-supportive hydrogel after dispersion by ultrasonication while $O_1$-$O_4$ remain insoluble and $O_6$ dissolves to form a viscous solution. This suggests that $O_5$ reaches a state of optimal fiber length and entanglement to create a stable hydrogel. FIG. 4A shows the CD spectra of aqueous 1 wt. % (4.2 mM) $O_5$ peptide solution in 149 mM sucrose and 0.5×HBSS. SEM analysis of the resulting hydrogel reveals a high-density nanofiber network (FIG. 4B). The viscoelastic properties of the $O_5$ hydrogel were analyzed by oscillatory rheology, and a storage modulus (G') of 23.3±8.7 Pa and a loss modulus (G") of 1.7±0.5 Pa were found. The low G' value compared to previously studied MDPs (Aulisa et al., 2009), which are typically in the range of 100-400 Pa, indicates that this material is a relatively compliant and flexible gel, which is also confirmed by the frequency sweep (FIG. 12). The $O_5$ peptide hydrogel exhibits liquid behavior when high strain is applied, while having a very rapid recovery of approximately 92% of its initial storage modulus 1 minute after the strain is released (FIG. 4D), making this supramolecular material easily injectable because of its shear thinning and shear recovery properties. In comparison, charged MDPs typically show a slower shear recovery of approximately 80% in the same time frame and require approximately 10 minutes to reach 90% recovery (Aulisa et al., 2009).

Example 5—Cytocompatibility of $O_5$ Peptide Hydrogel

Figure 5A:
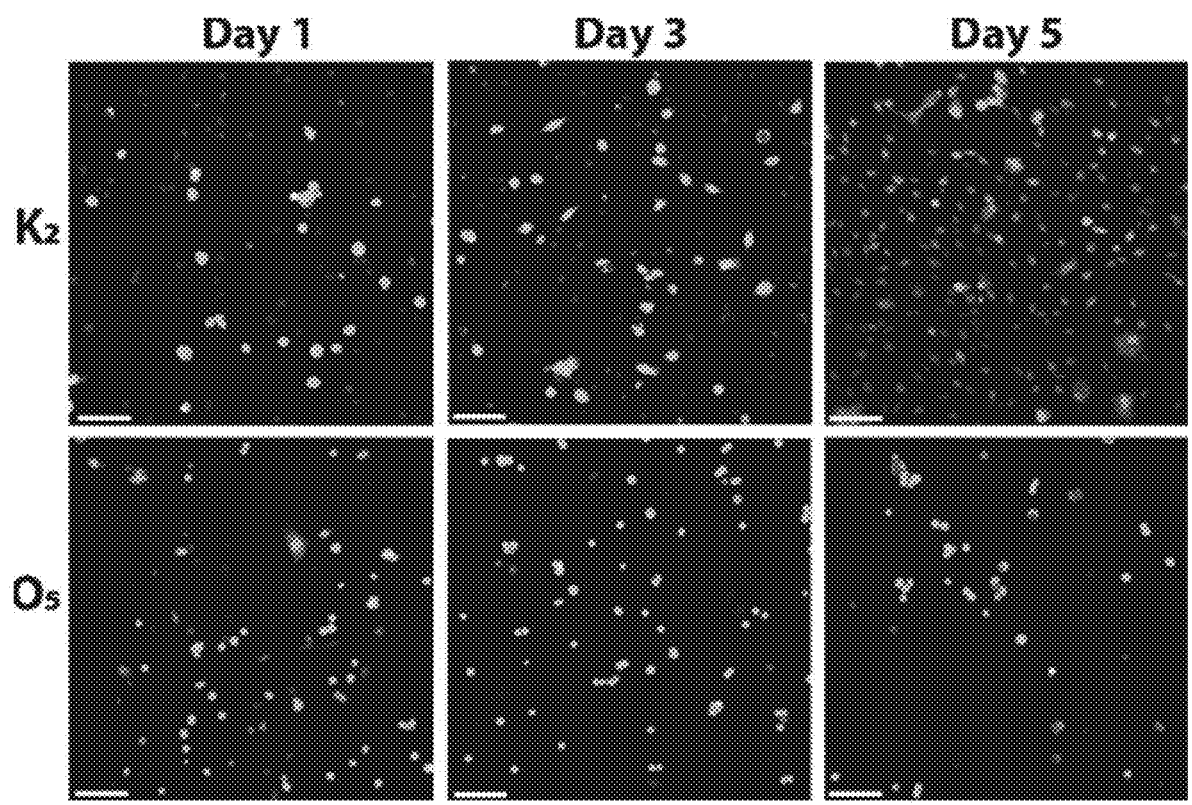
Figure 13:
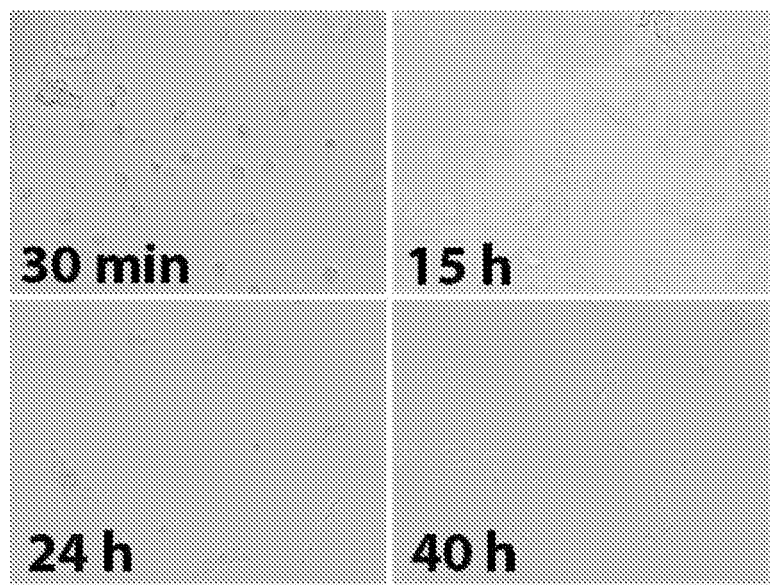
FIG. 13. NIH-3T3 fibroblasts cultured in 1 wt. % $O_5$ for 5 days grow and proliferate again after harvesting from the peptide scaffold. 30 min after harvesting, the cells are still in the balled-up morphology, but they start adhering to the tissue plastic and recover.

Former MDP hydrogels, particularly lysine-based peptides, have shown great promise for their use as biomaterials in part because of their cytocompatibility (Moore & Hartgerink, 2017). To study the effect of using non-ionic $O_5$ flanking domains on cell compatibility, 3D culture of NIH-3T3 fibroblasts was performed in $O_5$ peptide hydrogel and compared to culture in the positively charged $K_2$ peptide. Cell viability was evaluated using a Calcein-AM and Ethidium homodimer-1 test (FIG. 5). At day 1, approximately 20% of cells are viable in $K_2$ hydrogel, whereas for $O_5$ hydrogel, almost 70% survive after encapsulation (FIGS. 5A-D). At day 3, these levels are relatively unchanged. By day 5, fibroblasts are growing and reproducing in the positively charged $K_2$ hydrogel, achieving a similar percentage of viable cells as $O_5$ hydrogel. Overall, $K_2$ is observed to be somewhat cytotoxic during the first days of cell culture, likely due to the high density of positively charged amines. However, cells recover and can attach and proliferate within the gel, and by day 5 cell density is significantly higher than days 1 and 3 (FIG. 5E). On the other hand, fibroblasts encapsulated in the $O_5$ hydrogel show good initial viability, which remains constant throughout the experiment (FIG. 5D). Despite high and consistent cell viability in $O_5$ over the course of this study, the encapsulated fibroblasts are not observed to proliferate. Cells encapsulated in $O_5$ gel do not spread and adhere to the material like in $K_2$, but instead they remain "balled up" as shown in FIGS. 5B-C. Generally, this balled-up morphology represents imminent cell death or apoptosis (Saraste & Pulkki, 2000), where cells die from 12 to 24 h after initiating this process (Saraste, 1999; Messam & Pittman, 1998). Yet, cells in the neutral MDP preserve this morphology through day 5 (120 h) and show green fluorescence derived from Calcein AM, indicating an intact membrane and cell survival. Cultured cells displaying this balled-up morphology recover, grow, and proliferate when extracted from the $O_5$ peptide hydrogel after 5 days of culture (FIG. 13). All these observations suggest that fibroblasts cultured in $O_5$ may be induced to enter a quiescent state when encapsulated within the hydrogel. The ability of $O_5$ hydrogel to keep cells alive without proliferation is a promising result with potential applications for the use of this material in cell preservation. The differences in cell viability, morphology, and proliferation are all indicators of the substantial differences induced by fibers with similar morphology but with different charge.

Example 6—In Vivo Host Response to $O_5$ Peptide Hydrogel

Figure 14A:
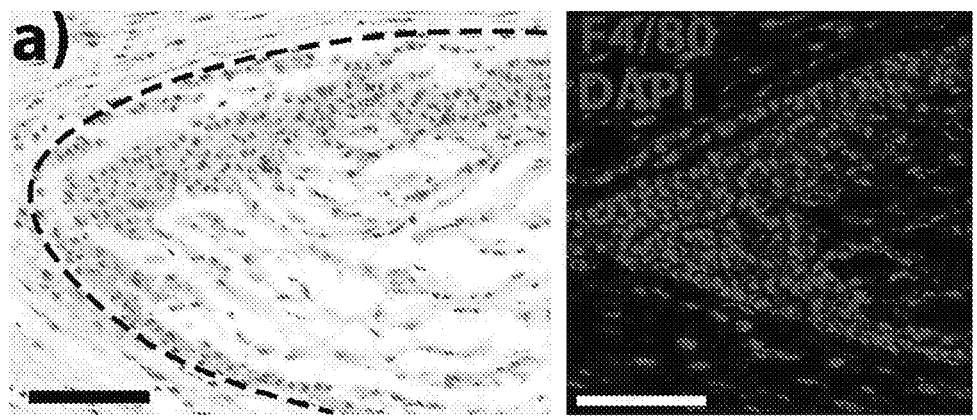
FIGS. 14A-C. H&E and immunofluorescent staining of subcutaneous implants of $O_5$ hydrogel.
Figure 14B:
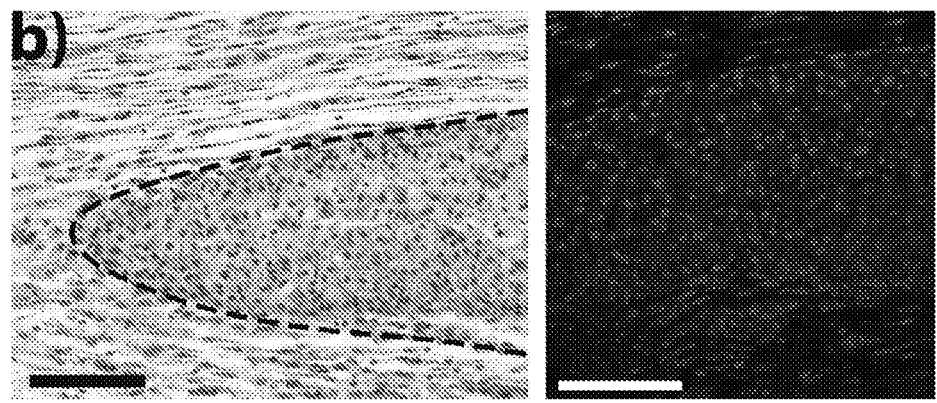
Figure 14C:
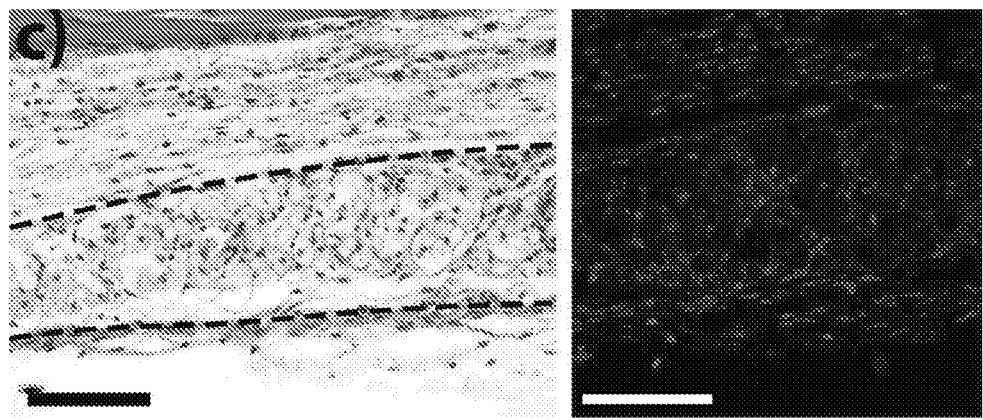
Figure 15A:
FIGS. 15A-C. H&E staining of $O_5(SL)_6O_5$ implants at day 3 (FIG. 15A), 7 (FIG. 15B), and 14 (FIG. 15C) after injection in a subcutaneous mouse model. Implant is degraded over time and size decreases. Scale bar: 1 mm.
Figure 15B:
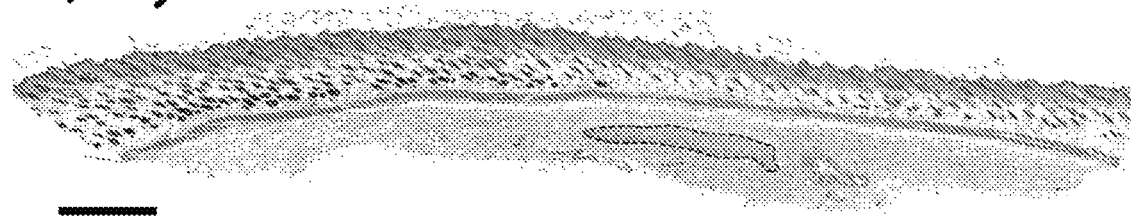
Figure 15C:
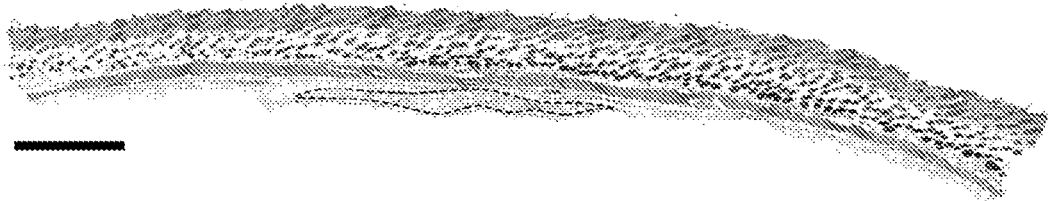

To investigate the application of this peptide-based material in regenerative medicine, the host response to $O_5$ peptide hydrogel was evaluated in mice using a subcutaneous injection model. The injected hydrogel boluses were examined at 3, 7, and 14 days after injection. FIGS. 14A-C shows histological sections of the implants stained with Hematoxylin & Eosin and fluorescent immunostaining for F4/80+ macrophages. At day 3 (FIG. 14A), F4/80+ macrophages have infiltrated the periphery of the material, while some are migrating to the core. By day 7 (FIG. 14B), macrophages have completely infiltrated the implant. A decrease in the implant size suggests that the $O_5$ hydrogel is degrading (FIGS. 15A-C). By day 14 (FIG. 14C) the hydrogel is almost completely degraded, with fewer macrophages present. Additionally, natural collagen is observed as the material is remodeled into natural tissue (FIGS. 16A-C). Compared to $K_2$ hydrogel, the neutral MDP $O_5$ elicited a weaker inflammatory response and did not promote vascularization or innervation (Moore et al., 2018). However, in contrast with other neutral polymers, such as PEG, the $O_5$ hydrogel promotes rapid cellular infiltration, is fully degradable and is not fibrously encapsulated (Lynn et al., 2009), demonstrating that it has achieved some of the "stealth" characteristics associated with PEG materials while also maintaining the ability to interact with living systems.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,004,681
U.S. Pat. No. 8,099,297
U.S. Pat. Appln. Publn. 2009/0305325
U.S. Pat. Appln. Publn. 2005/0106554
U.S. Pat. Appln. Publn. 2005/0277107
U.S. Pat. Appln. Publn. 2017/0335287
Aggeli et al., J. Am. Chem. Soc. 2003, 125, 9619-9628.
Aulisa et al., Biomacromolecules 2009, 10, 2694-2698.
Bakota et al., Biomacromolecules 2013, 14, 1370-1378.
Bankwell et al., Nat. Mater. 2009, 8, 596-600.
Blau, Curr. Opin. Colloid Interface Sci. 2013, 18, 481-492.
Chockalingam et al., Protein Eng. Des. Sel. 2007, 20, 155-161.
Collier et al., J. Am. Chem. Soc. 2001, 123, 9463-9464.
Cormier et al., ACS Nano 2013, 7, 7562-7572.
Dong et al., J. Am. Chem. Soc. 2007, 129, 12468-12472.
Fischer et al., Biomaterials 2003, 24, 1121-1131.
Habibi et al., Nano Today 2016, 11, 41-60.
Hanna & Hubel, Preservation of Stem Cells. Organogenesis 2009, 5(3), 134-137.
Hartgerink et al., J. Am. Chem. Soc. 1996, 118, 43-50.
Hartgerink et al., Science 2001, 294, 1684-1688.
Holmes et al., Proc. Natl. Acad. Sci. U.S.A. 2000, 97, 6728-6733.
Hunt, Transfus. Med. Hemotherapy 2011, 38(2), 107-123.
Kadlecova et al., Biomacromolecules 2012, 13, 3127-3137.
Leach et al., Biomaterials 2018, 163, 67-75.
Li et al., Chem. Rev. 2015, 115, 8564-8608.
Li & Hartgerink, J. Am. Chem. Soc. 2017, 139, 8044-8050.
Lutolf & Hubbell, Nat. Biotechnol. 2005, 23, 47-55.

Lynn et al., J. Biomed. Mater. Res. Part A 2009, 93A, 941-953.
Mazia et al., J. Cell 1975, 66, 198-200.
Menges, 2017, Version 1.2.7.
Messam & Pittman, Exp. Cell Res. 1998, 238, 389-398.
Meyers & Grinstaff, Chem. Rev. 2012, 112, 1615-1632.
Micklitsch et al., Angew. Chemie—Int. Ed. 2011, 50, 1577-1579.
Moore et al., Biomaterials 2018, 161, 154-163.
Moore & Hartgerink, Acc. Chem. Res. 2017, 50, 714-722.
Myers et al., Protein Sci. 1998, 7, 383-388.
Nisbet & Williams, Biointerphases 2012, 7, 1-14.
Pochan et al., J. Am. Chem. Soc. 2003, 125, 11802-11803.
Powers et al., Angew. Chemie-International Ed. 2002, 41, 127-130.
Rad-Malekshahi et al., Bioconjug. Chem. 2016, 27, 3-18.
Roccatano et al., Proc. Natl. Acad. Sci. 2002, 99, 12179-12184.
Saha & Jaenisch, Cell Stem Cell 2009, 5(6), 584-595.
Saraste, Herz 1999, 24, 189-195.
Saraste & Pulkki, Cardiovasc. Res. 2000, 45, 528-537.
Schneider et al., J. Am. Chem. Soc. 2002, 124, 15030-15037.
Sonnichsen et al., Biochemistry 1992, 31, 8790-8798.
Stathopulos et al., Protein Sci. 2004, 13, 3017-3027.
Stupp et al., Science 1997, 276, 384-389.
Veiga et al., Biomaterials 2012, 33, 8907-8916.
Webber et al., Nat. Mater. 2015, 15, 13-26.
Zhu, Biomaterials 2010, 31, 4639-4656.

The invention claimed is:

1. A composition comprising a plurality of peptides; wherein each peptide of the plurality of peptides consists of a first domain, a second domain, and a third domain; wherein the first and third domain are each $X_m$, wherein m is 5 and X is 3'-hydroxyproline or 4'-hydroxyproline; wherein the first domain is positioned at the N-terminal end of the second domain; wherein the third domain is positioned at the C-terminal end of the second domain; wherein the second domain comprises (SerLeu)$_6$; and wherein the peptides are N-terminally acetylated.

2. The composition of claim 1, wherein the amino acid sequence of each peptide consists of SEQ ID NO: 5.

3. The composition of claim 1, wherein the peptides further comprise a biologically active peptide mimic.

4. The composition of claim 3, wherein the biologically active peptide mimic has a sequence selected from the group consisting of one of SEQ ID NOs: 10-20.

5. The composition of claim 1, wherein the composition is lyophilized.

6. A nanofiber comprising a plurality of peptides according to claim 1.

7. A hydrogel comprising a plurality of peptides according to claim 1.

* * * * *

SEQUENCE LISTING

```
<160> NUMBER OF SEQ ID NOS: 20

<210> SEQ ID NO 1
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Xaa represents hydroxyproline
<220> FEATURE:
<221> NAME/KEY: MOD_RES
<222> LOCATION: (14)..(14)
<223> OTHER INFORMATION: Xaa represents hydroxyproline

<400> SEQUENCE: 1

Xaa Ser Leu Ser Leu Ser Leu Ser Leu Ser Leu Ser Leu Xaa
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(2)
<223> OTHER INFORMATION: Xaa represents hydroxyproline
<220> FEATURE:
<221> NAME/KEY: MOD_RES
<222> LOCATION: (15)..(16)
<223> OTHER INFORMATION: Xaa represents hydroxyproline

<400> SEQUENCE: 2

Xaa Xaa Ser Leu Ser Leu Ser Leu Ser Leu Ser Leu Ser Leu Xaa Xaa
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(3)
<223> OTHER INFORMATION: Xaa represents hydroxyproline
<220> FEATURE:
<221> NAME/KEY: MOD_RES
<222> LOCATION: (16)..(18)
<223> OTHER INFORMATION: Xaa represents hydroxyproline
```

<400> SEQUENCE: 3

Xaa Xaa Xaa Ser Leu Ser Leu Ser Leu Ser Leu Ser Leu Xaa
1               5                   10                  15

Xaa Xaa

<210> SEQ ID NO 4
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(4)
<223> OTHER INFORMATION: Xaa represents hydroxyproline
<220> FEATURE:
<221> NAME/KEY: MOD_RES
<222> LOCATION: (17)..(20)
<223> OTHER INFORMATION: Xaa represents hydroxyproline

<400> SEQUENCE: 4

Xaa Xaa Xaa Xaa Ser Leu Ser Leu Ser Leu Ser Leu Ser Leu
1               5                   10                  15

Xaa Xaa Xaa Xaa
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(5)
<223> OTHER INFORMATION: Xaa represents hydroxyproline
<220> FEATURE:
<221> NAME/KEY: MOD_RES
<222> LOCATION: (18)..(22)
<223> OTHER INFORMATION: Xaa represents hydroxyproline

<400> SEQUENCE: 5

Xaa Xaa Xaa Xaa Xaa Ser Leu Ser Leu Ser Leu Ser Leu Ser
1               5                   10                  15

Leu Xaa Xaa Xaa Xaa Xaa
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(6)
<223> OTHER INFORMATION: Xaa represents hydroxyproline
<220> FEATURE:
<221> NAME/KEY: MOD_RES
<222> LOCATION: (19)..(24)
<223> OTHER INFORMATION: Xaa represents hydroxyproline

<400> SEQUENCE: 6

Xaa Xaa Xaa Xaa Xaa Xaa Ser Leu Ser Leu Ser Leu Ser Leu
1               5                   10                  15

Ser Leu Xaa Xaa Xaa Xaa Xaa Xaa
            20

```
<210> SEQ ID NO 7
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 7

Lys Lys Ser Leu Ser Leu Ser Leu Ser Leu Ser Leu Ser Leu Lys Lys
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 8

Glu Glu Ser Leu Ser Leu Ser Leu Ser Leu Ser Leu Ser Leu Glu Glu
1               5                   10                  15

<210> SEQ ID NO 9
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(6)
<223> OTHER INFORMATION: Xaa represents hydroxyproline

<400> SEQUENCE: 9

Xaa Xaa Xaa Xaa Xaa Xaa
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 10

Arg Gly Asp Ser
1

<210> SEQ ID NO 11
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 11

Ile Lys Val Ala Val
1               5

<210> SEQ ID NO 12
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 12
```

```
Lys Asp Ile
1

<210> SEQ ID NO 13
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 13

Arg Asn Ile Ala Glu Ile Ile Lys Asp Ile
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 14

Val Phe Asp Asn Phe Val Leu Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 15

Asp Trp Ile Val Ala
1               5

<210> SEQ ID NO 16
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 16

Ala Gln Phe His Arg His Lys Gln Leu Ile Arg Phe Leu Lys Arg Ala
1               5                   10                  15

<210> SEQ ID NO 17
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 17

Arg Glu Leu Arg Tyr Leu Arg Arg Ala
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 18

Phe Leu Pro Ala Ser Gly Leu
```

```
<210> SEQ ID NO 19
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 19

Glu Ser Pro Leu Lys Arg Gln
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 20

Asp Pro His Ile Lys Leu Gln Leu Gln Ala Glu
1               5                   10
```